US009889058B2

(12) United States Patent
Horst et al.

(10) Patent No.: US 9,889,058 B2
(45) Date of Patent: Feb. 13, 2018

(54) ORTHOTIC DEVICE DRIVE SYSTEM AND METHOD

(71) Applicant: ALTERG, INC., Fremont, CA (US)

(72) Inventors: Robert W. Horst, San Jose, CA (US); Richard R. Marcus, Mountain View, CA (US)

(73) Assignee: AlterG, Inc., Fremont, CA (US)

( * ) Notice: Subject to any disclaimer, the term of this patent is extended or adjusted under 35 U.S.C. 154(b) by 288 days.

(21) Appl. No.: 14/769,119

(22) PCT Filed: Mar. 13, 2014

(86) PCT No.: PCT/US2014/026041
§ 371 (c)(1),
(2) Date: Aug. 20, 2015

(87) PCT Pub. No.: WO2014/151584
PCT Pub. Date: Sep. 25, 2014

(65) Prior Publication Data
US 2015/0374573 A1    Dec. 31, 2015

Related U.S. Application Data

(60) Provisional application No. 61/798,101, filed on Mar. 15, 2013.

(51) Int. Cl.
*A61H 1/02* (2006.01)
*A61H 3/00* (2006.01)
(Continued)

(52) U.S. Cl.
CPC .............. *A61H 1/024* (2013.01); *A61F 5/013* (2013.01); *A61F 5/0125* (2013.01);
(Continued)

(58) Field of Classification Search
CPC ........ A61H 1/024; A61H 1/0277; A61H 3/00; A61H 2201/0184; A61H 2201/1215;
(Continued)

(56) References Cited

U.S. PATENT DOCUMENTS 1,286,482 A    12/1918  Yoder
1,366,904 A    2/1921   Davis
(Continued)

FOREIGN PATENT DOCUMENTS

EP    1138286 A2    10/2001
EP    1410780 A1    4/2004
(Continued)

OTHER PUBLICATIONS

Advanced Mechatronics Lab (Univ. of Tokyo); Dual Excitation Multiphase Electrostatic Drive (DEMED); http://www.intellect.pe.u-tokyo.ac.jp/research/es_motor/demed_e.html; pp. 1-5; (printed) Nov. 21, 2002.

(Continued)

*Primary Examiner* — Ophelia A Hawthorne
(74) *Attorney, Agent, or Firm* — Shay Glenn LLP

(57) ABSTRACT

An orthosis includes a first portion and a second portion configured to attach on opposite sides of a joint. An actuator is configured to apply a force between the first and second portions. The actuator includes a first spool and a second spool rotatably mounted to the first portion. An output pulley is mounted to the second portion. A belt has a first end wrapped around the first spool, a second end wrapped around the second spool, and a mid-portion wrapped around the output pulley. The actuator is configured to rotate the first and second spools. The rotation of the first spool pulls the belt a given length, and the rotation of the second spool feeds (Continued)

the belt less than the given length, so as to pull the output pulley towards the first portion to pull the second portion towards the first portion.

37 Claims, 19 Drawing Sheets

(51) Int. Cl.
    *A61F 5/01*     (2006.01)
    *F16H 19/06*     (2006.01)

(52) U.S. Cl.
    CPC ............ *A61H 1/0277* (2013.01); *A61H 3/00* (2013.01); *F16H 19/0631* (2013.01); *A61F 2005/0155* (2013.01); *A61F 2005/0188* (2013.01); *A61H 2201/0184* (2013.01); *A61H 2201/1215* (2013.01); *A61H 2201/1463* (2013.01); *A61H 2201/164* (2013.01); *A61H 2201/165* (2013.01); *A61H 2201/501* (2013.01); *A61H 2201/5061* (2013.01); *A61H 2201/5064* (2013.01); *A61H 2201/5069* (2013.01); *A61H 2201/5071* (2013.01); *A61H 2201/5092* (2013.01); *A61H 2230/605* (2013.01); *F16H 2019/0695* (2013.01)

(58) Field of Classification Search
    CPC ...... A61H 2201/1463; A61H 2201/164; A61H 2201/165; A61H 2201/501; A61H 2201/5061; A61H 2201/5064; A61H 2201/5069; A61H 2201/5071; A61H 2201/5092; A61H 2230/605; A61F 5/0125; A61F 5/013; A61F 2005/0155; A61F 2005/0188; A61F 5/0123; A61F 2005/0139; A61F 5/0102; A61F 2005/0167; F16H 19/0631; F16H 2019/0695

See application file for complete search history.

(56) References Cited

U.S. PATENT DOCUMENTS

| | | |
|---|---|---|
| 1,391,290 A | 9/1921 | Welffens |
| 1,513,473 A | 10/1924 | Ackerman |
| 1,739,053 A | 12/1929 | Wilhelm |
| 1,847,720 A | 3/1932 | Marcellis |
| 2,169,813 A | 8/1939 | Parkin |
| 3,059,490 A | 10/1962 | McDuffie |
| 3,200,666 A | 8/1965 | Schrodt et al. |
| 3,358,678 A | 12/1967 | Kultsar |
| 3,398,248 A | 8/1968 | Klauss et al. |
| 3,402,942 A | 9/1968 | Shimano et al. |
| 3,631,542 A | 1/1972 | Potter |
| 3,641,843 A | 2/1972 | Lemmens |
| 3,863,512 A | 2/1975 | Crawley |
| 3,899,383 A | 8/1975 | Schultz et al. |
| 3,925,131 A | 12/1975 | Krause |
| 3,976,057 A | 8/1976 | Barclay |
| 4,273,113 A | 6/1981 | Hofstein |
| 4,474,176 A | 10/1984 | Farris et al. |
| 4,507,104 A | 3/1985 | Clark et al. |
| 4,538,595 A | 9/1985 | Hajianpour |
| 4,549,555 A | 10/1985 | Fraser et al. |
| 4,588,040 A | 5/1986 | Albright, Jr. et al. |
| 4,647,918 A | 3/1987 | Goforth |
| 4,649,488 A | 3/1987 | Osanai et al. |
| 4,665,899 A | 5/1987 | Farris et al. |
| 4,678,354 A | 7/1987 | Olsen |
| 4,679,548 A | 7/1987 | Pecheux |
| 4,691,694 A | 9/1987 | Boyd et al. |
| 4,697,808 A | 10/1987 | Larson et al. |
| 4,731,044 A | 3/1988 | Mott |
| 4,745,930 A | 5/1988 | Confer |
| 4,754,185 A | 6/1988 | Gabriel et al. |
| 4,796,631 A | 1/1989 | Grigoryev |
| 4,801,138 A | 1/1989 | Airy et al. |
| 4,807,874 A | 2/1989 | Little |
| 4,814,661 A | 3/1989 | Ratzlaff et al. |
| 4,825,852 A | 5/1989 | Genovese et al. |
| 4,872,665 A | 10/1989 | Chareire |
| 4,878,663 A | 11/1989 | Luquette |
| 4,883,445 A | 11/1989 | Gomoll et al. |
| 4,922,925 A | 5/1990 | Crandall et al. |
| 4,934,694 A | 6/1990 | McIntosh |
| 4,944,713 A | 7/1990 | Salerno |
| 4,953,543 A | 9/1990 | Grim et al. |
| 4,981,116 A | 1/1991 | Trinquard |
| 4,983,146 A | 1/1991 | Charles et al. |
| 5,020,790 A | 6/1991 | Beard et al. |
| 5,046,375 A | 9/1991 | Salisbury et al. |
| 5,052,681 A | 10/1991 | Williams |
| 5,078,152 A | 1/1992 | Bond et al. |
| 5,117,814 A | 6/1992 | Luttrell et al. |
| 5,170,776 A | 12/1992 | Pecheux |
| 5,170,777 A | 12/1992 | Reddy et al. |
| 5,195,617 A | 3/1993 | Clemens |
| 5,203,321 A | 4/1993 | Donovan et al. |
| 5,209,223 A | 5/1993 | McGorry et al. |
| 5,213,094 A * | 5/1993 | Bonutti ................ A61F 5/0123 601/33 |
| 5,239,222 A | 8/1993 | Higuchi et al. |
| 5,241,952 A | 9/1993 | Ortiz |
| 5,282,460 A | 2/1994 | Boldt |
| 5,303,716 A | 4/1994 | Mason et al. |
| 5,313,968 A | 5/1994 | Logan et al. |
| 5,345,834 A | 9/1994 | Hayashi |
| 5,358,468 A | 10/1994 | Longo et al. |
| 5,378,954 A | 1/1995 | Higuchi et al. |
| 5,395,303 A | 3/1995 | Bonutti et al. |
| 5,399,147 A | 3/1995 | Kaiser |
| 5,410,488 A | 4/1995 | Andersen |
| 5,421,798 A | 6/1995 | Bond et al. |
| 5,440,945 A | 8/1995 | Penn |
| 5,448,124 A | 9/1995 | Higuchi et al. |
| 5,463,526 A | 10/1995 | Mundt |
| 5,476,441 A | 12/1995 | Durfee et al. |
| 5,509,894 A | 4/1996 | Mason et al. |
| 5,520,627 A | 5/1996 | Malewicz |
| 5,525,642 A | 6/1996 | Cipriano et al. |
| 5,534,740 A | 7/1996 | Higuchi et al. |
| 5,541,465 A | 7/1996 | Higuchi et al. |
| 5,573,088 A | 11/1996 | Daniels |
| 5,582,579 A | 12/1996 | Chism et al. |
| 5,585,683 A | 12/1996 | Higuchi et al. |
| 5,608,599 A | 3/1997 | Goldman |
| 5,624,390 A | 4/1997 | Van Dyne |
| 5,653,680 A | 8/1997 | Cruz |
| 5,662,594 A | 9/1997 | Rosenblatt |
| 5,662,693 A | 9/1997 | Johnson et al. |
| 5,674,262 A | 10/1997 | Tumey |
| 5,678,448 A | 10/1997 | Fullen et al. |
| 5,683,351 A | 11/1997 | Kaiser et al. |
| 5,695,859 A | 12/1997 | Burgess |
| 5,704,440 A | 1/1998 | Urban et al. |
| 5,708,319 A | 1/1998 | Ban et al. |
| 5,728,017 A | 3/1998 | Bellio et al. |
| 5,746,684 A | 5/1998 | Jordan |
| 5,746,704 A | 5/1998 | Schenck et al. |
| 5,755,303 A | 5/1998 | Yamamoto et al. |
| 5,789,843 A | 8/1998 | Higuchi et al. |
| 5,833,257 A | 11/1998 | Kohlheb et al. |
| 5,865,770 A | 2/1999 | Schectman |
| 5,916,689 A | 6/1999 | Collins et al. |
| 5,931,756 A | 8/1999 | Ohsono et al. |
| 5,976,063 A | 11/1999 | Joutras et al. |
| 6,001,075 A | 12/1999 | Clemens et al. |
| 6,030,351 A | 2/2000 | Schmidt et al. |
| 6,033,330 A | 3/2000 | Wong et al. |
| 6,033,370 A | 3/2000 | Reinbold et al. |
| 6,062,096 A | 5/2000 | Lester |
| 6,119,539 A | 9/2000 | Papanicolaou |

(56) References Cited

U.S. PATENT DOCUMENTS

| | | | |
|---|---|---|---|
| 6,146,341 A | 11/2000 | Sato et al. |
| 6,149,612 A | 11/2000 | Schnapp et al. |
| 6,162,189 A | 12/2000 | Girone et al. |
| 6,183,431 B1 | 2/2001 | Gach, Jr. |
| 6,217,532 B1 | 4/2001 | Blanchard et al. |
| 6,221,032 B1 | 4/2001 | Blanchard et al. |
| 6,290,662 B1 | 9/2001 | Morris et al. |
| 6,314,835 B1 | 11/2001 | Lascelles et al. |
| 6,375,619 B1 | 4/2002 | Ohdachi |
| 6,387,066 B1 | 5/2002 | Whiteside |
| 6,440,093 B1 | 8/2002 | McEwen et al. |
| 6,472,795 B2 | 10/2002 | Hirose et al. |
| 6,494,798 B1 | 12/2002 | Onogi |
| 6,500,138 B1 | 12/2002 | Irby et al. |
| 6,517,503 B1 | 2/2003 | Naft et al. |
| 6,525,446 B1 | 2/2003 | Yasuda et al. |
| 6,527,671 B2 | 3/2003 | Paalasmaa et al. |
| 6,533,742 B1 | 3/2003 | Gach, Jr. |
| 6,537,175 B1 | 3/2003 | Blood |
| 6,554,773 B1 | 4/2003 | Nissila et al. |
| 6,572,558 B2 | 6/2003 | Masakov et al. |
| 6,599,255 B2 | 7/2003 | Zhang |
| 6,659,910 B2 | 12/2003 | Gu et al. |
| 6,666,796 B1 | 12/2003 | MacCready, Jr. |
| 6,689,075 B2 | 2/2004 | West |
| 6,694,833 B2 | 2/2004 | Hoehn et al. |
| 6,709,411 B1 | 3/2004 | Olinger |
| 6,796,926 B2 | 9/2004 | Reinkensmeyer et al. |
| 6,805,677 B2 | 10/2004 | Simmons |
| 6,821,262 B1 | 11/2004 | Muse et al. |
| 6,827,579 B2 | 12/2004 | Burdea et al. |
| 6,836,744 B1 | 12/2004 | Asphahani et al. |
| 6,872,187 B1 | 3/2005 | Stark et al. |
| 6,878,122 B2 | 4/2005 | Cordo |
| 6,936,994 B1 | 8/2005 | Gimlan |
| 6,966,882 B2 | 11/2005 | Horst |
| 7,041,069 B2 | 5/2006 | West |
| 7,124,321 B2 | 10/2006 | Garnett et al. |
| 7,137,938 B2 | 11/2006 | Gottlieb |
| 7,171,331 B2 | 1/2007 | Vock et al. |
| 7,190,141 B1 | 3/2007 | Ashrafiuon et al. |
| 7,192,401 B2 | 3/2007 | Saalasti et al. |
| 7,217,247 B2 | 5/2007 | Dariush et al. |
| 7,239,065 B2 | 7/2007 | Horst |
| 7,252,644 B2 | 8/2007 | Dewald et al. |
| 7,309,320 B2 | 12/2007 | Schmehl |
| 7,324,841 B2 | 1/2008 | Reho et al. |
| 7,365,463 B2 | 4/2008 | Horst et al. |
| 7,410,471 B1 | 8/2008 | Campbell et al. |
| 7,416,537 B1 | 8/2008 | Stark et al. |
| 7,431,707 B2 | 10/2008 | Ikeuchi |
| 7,457,724 B2 | 11/2008 | Vock et al. |
| 7,458,922 B2 | 12/2008 | Pisciottano |
| 7,537,573 B2 | 5/2009 | Horst |
| 7,559,909 B2 | 7/2009 | Katoh et al. |
| 7,578,799 B2 | 8/2009 | Thorsteinsson et al. |
| 7,648,436 B2 * | 1/2010 | Horst ............... F16H 19/06 474/117 |
| 7,731,670 B2 | 6/2010 | Aguirre-Ollinger et al. |
| 7,833,178 B2 | 11/2010 | Lee et al. |
| 7,880,345 B2 | 2/2011 | Hoffmann et al. |
| 7,998,092 B2 | 8/2011 | Avni et al. |
| 8,052,629 B2 | 11/2011 | Smith et al. |
| 8,058,823 B2 | 11/2011 | Horst et al. |
| 8,167,829 B2 | 5/2012 | Sterling et al. |
| 8,274,244 B2 | 9/2012 | Horst et al. |
| 8,353,854 B2 | 1/2013 | Horst et al. |
| 8,639,455 B2 | 1/2014 | Horst et al. |
| 8,679,040 B2 | 3/2014 | Horst |
| 8,771,210 B2 | 7/2014 | Smith et al. |
| 9,131,873 B2 | 9/2015 | Horst et al. |
| 2001/0029343 A1 | 10/2001 | Seto et al. |
| 2002/0029911 A1 | 3/2002 | Richards |
| 2002/0128552 A1 | 9/2002 | Nowlin et al. |
| 2003/0104886 A1 | 6/2003 | Gajewski |
| 2003/0120183 A1 | 6/2003 | Simmons |
| 2003/0184310 A1 | 10/2003 | Lurtz |
| 2003/0195638 A1 | 10/2003 | Kajitani et al. |
| 2003/0212356 A1 | 11/2003 | Scorvo |
| 2004/0015112 A1 | 1/2004 | Salutterback et al. |
| 2004/0049139 A1 | 3/2004 | Craciunescu |
| 2004/0054311 A1 | 3/2004 | Sterling |
| 2004/0078091 A1 | 4/2004 | Elkins |
| 2004/0106881 A1 | 6/2004 | McBean et al. |
| 2005/0014600 A1 | 1/2005 | Clauson |
| 2005/0085346 A1 | 4/2005 | Johnson |
| 2005/0085353 A1 | 4/2005 | Johnson |
| 2005/0101887 A1 | 5/2005 | Stark et al. |
| 2005/0151420 A1 | 7/2005 | Crombez et al. |
| 2005/0173994 A1 | 8/2005 | Pfister et al. |
| 2005/0210557 A1 | 9/2005 | Falconer |
| 2005/0221926 A1 | 10/2005 | Naude |
| 2005/0245849 A1 | 11/2005 | Cordo |
| 2005/0251067 A1 | 11/2005 | Terry |
| 2005/0253675 A1 | 11/2005 | Davison |
| 2005/0273022 A1 | 12/2005 | Diaz et al. |
| 2006/0004265 A1 | 1/2006 | Pulkkinen et al. |
| 2006/0046907 A1 | 3/2006 | Rastegar et al. |
| 2006/0069336 A1 | 3/2006 | Krebs et al. |
| 2006/0108954 A1 | 5/2006 | Sebille et al. |
| 2006/0132069 A1 | 6/2006 | Hemphill et al. |
| 2006/0157010 A1 | 7/2006 | Moriwaki et al. |
| 2006/0206045 A1 | 9/2006 | Townsend et al. |
| 2006/0249315 A1 | 11/2006 | Herr et al. |
| 2006/0251179 A1 | 11/2006 | Ghoshal |
| 2006/0293624 A1 | 12/2006 | Enzerink et al. |
| 2007/0015611 A1 | 1/2007 | Noble et al. |
| 2007/0038161 A1 | 2/2007 | Bonutti et al. |
| 2007/0055163 A1 | 3/2007 | Asada et al. |
| 2007/0093729 A1 | 4/2007 | Ewing |
| 2007/0105695 A1 | 5/2007 | Susta |
| 2007/0149899 A1 | 6/2007 | Shechtman et al. |
| 2007/0155557 A1 | 7/2007 | Horst et al. |
| 2007/0155558 A1 | 7/2007 | Horst et al. |
| 2007/0155560 A1 | 7/2007 | Horst et al. |
| 2007/0155588 A1 | 7/2007 | Stark et al. |
| 2007/0162152 A1 | 7/2007 | Herr et al. |
| 2007/0173747 A1 | 7/2007 | Knotts |
| 2007/0225620 A1 | 9/2007 | Carignan et al. |
| 2007/0248799 A1 | 10/2007 | DeAngelis et al. |
| 2007/0265534 A1 | 11/2007 | Martikka et al. |
| 2007/0270265 A1 | 11/2007 | Miller et al. |
| 2007/0287302 A1 | 12/2007 | Lindberg et al. |
| 2007/0287928 A1 | 12/2007 | Kiviniemi et al. |
| 2008/0039731 A1 | 2/2008 | McCombie et al. |
| 2008/0097269 A1 | 4/2008 | Weinberg et al. |
| 2008/0152463 A1 | 6/2008 | Chidambaram et al. |
| 2008/0177208 A1 | 7/2008 | Borschneck |
| 2008/0200994 A1 | 8/2008 | Colgate et al. |
| 2008/0234608 A1 | 9/2008 | Sankai |
| 2008/0281436 A1 | 11/2008 | Townsend et al. |
| 2009/0007983 A1 | 1/2009 | Healy |
| 2009/0036804 A1 | 2/2009 | Horst |
| 2009/0048686 A1 | 2/2009 | Ikeuchi et al. |
| 2009/0093353 A1 | 4/2009 | Weiner |
| 2009/0131839 A1 | 5/2009 | Yasuhara |
| 2009/0171469 A1 | 7/2009 | Thorsteinsson et al. |
| 2009/0235739 A1 | 9/2009 | Morris-Bamberg et al. |
| 2009/0260426 A1 | 10/2009 | Lieberman et al. |
| 2009/0265018 A1 | 10/2009 | Goldfarb et al. |
| 2009/0306548 A1 | 12/2009 | Bhugra et al. |
| 2010/0049102 A1 | 2/2010 | Yasuhara |
| 2010/0113986 A1 | 5/2010 | Ashihara et al. |
| 2010/0114329 A1 | 5/2010 | Casler et al. |
| 2010/0125229 A1 | 5/2010 | Rudolph et al. |
| 2010/0224844 A1 | 9/2010 | Boussaton et al. |
| 2010/0234775 A1 | 9/2010 | Yasuhara et al. |
| 2010/0256537 A1 | 10/2010 | Menga |
| 2010/0280628 A1 | 11/2010 | Sankai |
| 2010/0298746 A1 | 11/2010 | Shimizu et al. |
| 2010/0318006 A1 | 12/2010 | Horst |
| 2011/0012869 A1 | 1/2011 | Klinghult |
| 2011/0015498 A1 | 1/2011 | Mestrovic et al. |
| 2011/0175744 A1 | 7/2011 | Englert et al. |

(56) References Cited

U.S. PATENT DOCUMENTS

| | | | |
|---|---|---|---|
| 2012/0291564 | A1 | 11/2012 | Amos et al. |
| 2012/0297885 | A1 | 11/2012 | Hou et al. |
| 2012/0316475 | A1 | 12/2012 | Bhugra et al. |
| 2013/0079687 | A1 | 3/2013 | Horst et al. |
| 2013/0165817 | A1 | 6/2013 | Horst et al. |
| 2013/0261511 | A1 | 10/2013 | Smith et al. |
| 2013/0345601 | A1 | 12/2013 | Bhugra et al. |
| 2014/0207037 | A1 | 7/2014 | Horst |
| 2014/0323936 | A1 | 10/2014 | Smith et al. |

FOREIGN PATENT DOCUMENTS

| | | |
|---|---|---|
| JP | 63-136978 A | 6/1988 |
| JP | 02-275162 A | 11/1990 |
| JP | 04-104180 A | 4/1992 |
| JP | 05-038948 A | 2/1993 |
| JP | 05-260766 | 10/1993 |
| JP | 06-038551 A | 2/1994 |
| JP | 07-274540 A | 10/1995 |
| JP | 08-033360 A | 2/1996 |
| JP | 08-149858 | 6/1996 |
| JP | 08-154304 A | 6/1996 |
| JP | 09-133196 A | 5/1997 |
| JP | 09-261975 A | 10/1997 |
| JP | 2001-353675 A | 12/2001 |
| JP | 2002-191654 A | 7/2002 |
| WO | WO 90/11049 A1 | 10/1990 |
| WO | WO 03/088865 A2 | 10/2003 |
| WO | WO 2005/057054 A1 | 6/2005 |
| WO | WO 2007/027673 A2 | 3/2007 |
| WO | WO 2007/041303 A2 | 4/2007 |

OTHER PUBLICATIONS

Advanced Mechatronics Lab (Univ. of Tokyo); High-power electrostatic motor; http://www.intellect.pe.u-tokyo.ac.jp/research/es_motor/es_motor_e.html; pp. 1-2; (printed) Nov. 21, 2002.
Advanced Mechatronics Lab (Univ. of Tokyo); Pulse driven induction electrostatic motor; http://www.intellect.pe.u-tokyo.ac.jp/research/es_motor/pim_e.html; pp. 1-5; (printed) Nov. 21, 2002.
ASEL (Univ. of Delaware); Powered orthosis project; http://www.asel.udel.edu/robotics/orthosis/orthosis.html, 1 pg.; (update) Jan. 17, 1999.
British Tech. Group; Demonstration of energy saving in vehicles by integrating an infinitely variable transmission with an optimized petrol engine; prj. No. TR/00087/92; pp. 1-19; (version) Jul. 15, 1998.
Coronel et al; The Coronel effect positively infinitely variable transmission; U.C. Davis; No. 04CVT-51; pp. 1-8; (year of pub. sufficiently earlier than effective US filed and any foreign priority date) 2004.
Fitch, C. J.; Development of the electrostatic clutch; IBM Journal; pp. 49-56; Jan. 1957.
Frank, Andrew; Engine optimization concepts . . . ; U.C. Davis; No. 04CVT-56; pp. 1-12; (year of pub. sufficiently earlier than effective US filed and any foreign priority date) 2004.
Gongola et al.; Design of a PZT-actuated proportional drum brake; IEEE ASME Trans. on Mech.; vol. 4; No. 4; pp. 409-416; Dec. 1999.
Howard Leitch, PPT LTD.; Waveform Gearing; Motion System Design; pp. 33-35; Nov. 2002.
James et al.; Increasing power density in a full toroidal variator; 3rd Int'l. IIR-Symposium; Innovative Automotive Transmission; pp. 1-11; Dec. 2004.
Kawamoto et al.; Power assist system HAL-3 for GAIT disorder person; ICCHP 2002; LNCS 2398; pp. 196-203; Aug. 2002.
Kim et al.; On the energy efficiency of CVT-based mobile robots; Proc. 2000 IEEE; Int. Conf. on Robotics & Automation; pp. 1539-1544; San Francisco, CA; Apr. 2000.
Kluger et al.; An overview of current automatic, manual and continuously variable transmission efficiencies and their projected future improvements; Int. Congress and Expo. (No. 1999-1-1259); pp. 1-6; Detroit, MI; Mar. 1-4, 1999.
Krebs et al.; A paradigm shift for rehabilitation robotics; Eng. In Medicine and Biology Magazine, IEEE; vol. 27; Issue 4; pp. 61-70; Jul. 2008.
Misuraca et al.; Lower limb human enhancer; Int. Mech. Eng. Conf. and Expo.; New York, NY; pp. 1-7; Nov. 11-16, 2001.
Niino et al.; Electrostatic artificial muscle: compact, high-power linear actuators with multiple-layer structures; Proc. IEEE Workshop on Micro Electro Mechanical Systems; Oiso, Japan; pp. 130-135; Jan. 1994.
Nugent, James; Design and performance of an exponential roller gear . . . ; U.C. Davis; No. 04CVT-18; pp. 1-8; (year of pub. sufficiently earlier than effective US filed and any foreign priority date) 2004.
Ohhashi, Toshio et al.; Human perspiration measurement; Physiological Measurement; vol. 19; pp. 449-461; Nov. 1998.
Otto Bock Health Care; (3C100 C-Leg® System) Creating a new standard for prosthetic control; http://www.ottobockus.com/products/op_lower_cleg.asp; pp. 1-2; (printed) Nov. 22, 2002.
Otto Bock Health Care; (3C100 C-Leg® System) New generation leg system revolutionizes lower limb prostheses; http://www.ottobockus.com/products/op_lower_cleg4.asp; pp. 1-2; (printed) Nov. 22, 2002.
Otto Bock Health Care; Sensor Walk White Paper; ID No. 09031595.1; pp. 1-12; May 2009.
Patras et al.; Electro-rheological fluids in the design of clutch systems for robotic applications; IEEE; pp. 554-558; Nov. 11-13, 1992.
Powell et al.; Computer model for a parallel hybrid electric vehicle (PHEV) with CVT; Proc. AACC; pp. 1011-1015; Chicago, IL; Jun. 2000.
Shastri et al.; Comparison of energy consumption and power losses of a conventionally controlled CVT with a servo-hydraulic controlled CVT and with a belt and chain as the torque transmitting element; U.C. Davis; No. 04CVT-55; pp. 1-11; Sep. 2004.
Shriner's Hospitals; Your new orthosis; http://www.shrinershq.org/patientedu/orthosis.html; pp. 1-3; (printed) Nov. 22, 2002.
Takaki et al; Load-sensitive continuously variable transmission for powerful and inexpensive robot hands; IEEE; pp. 45-46; Nov. 2004.
Takesue et al.; Development and experiments of actuator using MR fluid; IEEE; pp. 1838-1843; Oct. 2000.
Townsend Design; Functional Bracing Solutions (AIR Townsend & Ultra AIR); http://www.townsenddesign.com/air.html; 2 pgs; (printed) Nov. 21, 2002.
Townsend Design; Functional Knee Bracing Solutions; http://www.townsenddesign.com/functional.html; pp. 1; (printed) Nov. 21, 2002.
Townsend Design; Patented Motion Hinge (Planes of Motion); http://www.townsenddesign.com/motion.html; pp. 1; (printed) Nov. 21, 2002.
Trimmer et al.; An operational harmonic electrostatic motor; IEEE; pp. 13-16; Feb. 1989.
Smith et al., U.S. Appl. No. 12/471,299 entitled "Therapy and mobility assistance system," filed May 22, 2009.
Bhugra, Kern; U.S. Appl. No. 12/363,567 entitled "System and method for controlling the joint motion of a user based on a measured physiological property," filed Jan. 30, 2009.
Horst et al.; U.S. Appl. No. 14/932,796 entitled "Multi-mode active orthotic sensor," filed Nov. 4, 2015.

* cited by examiner

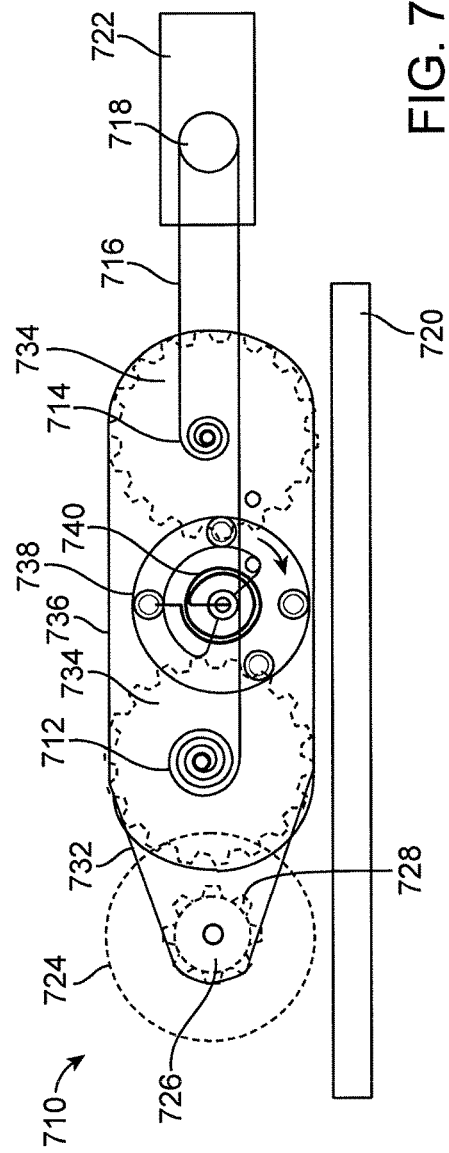
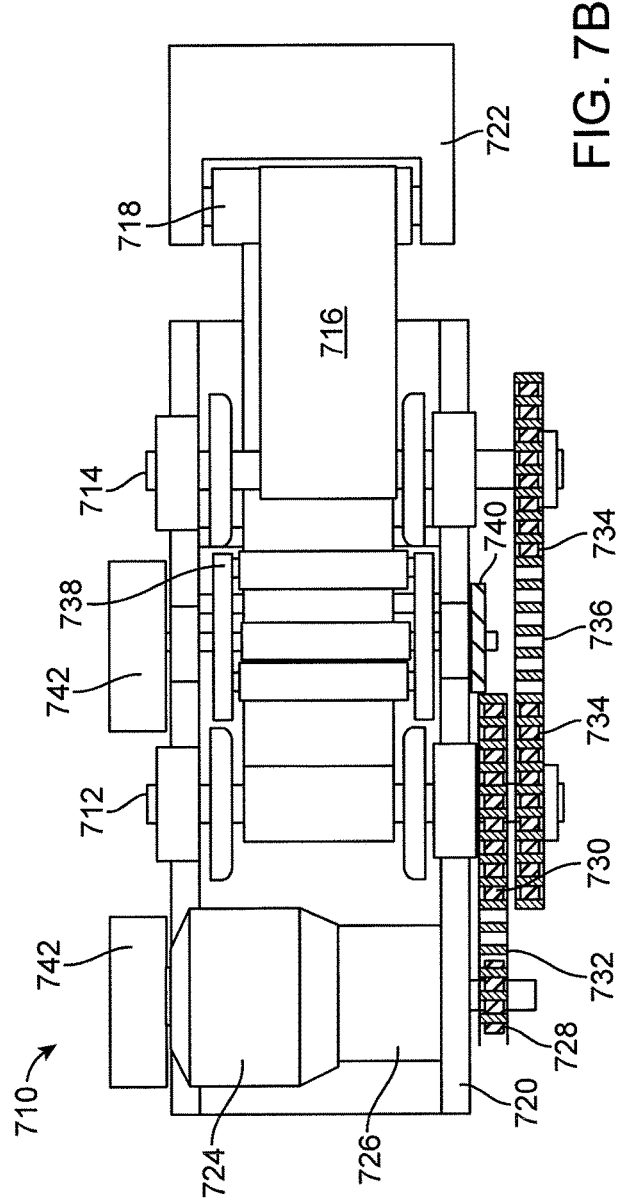
FIG. 7A
FIG. 7B

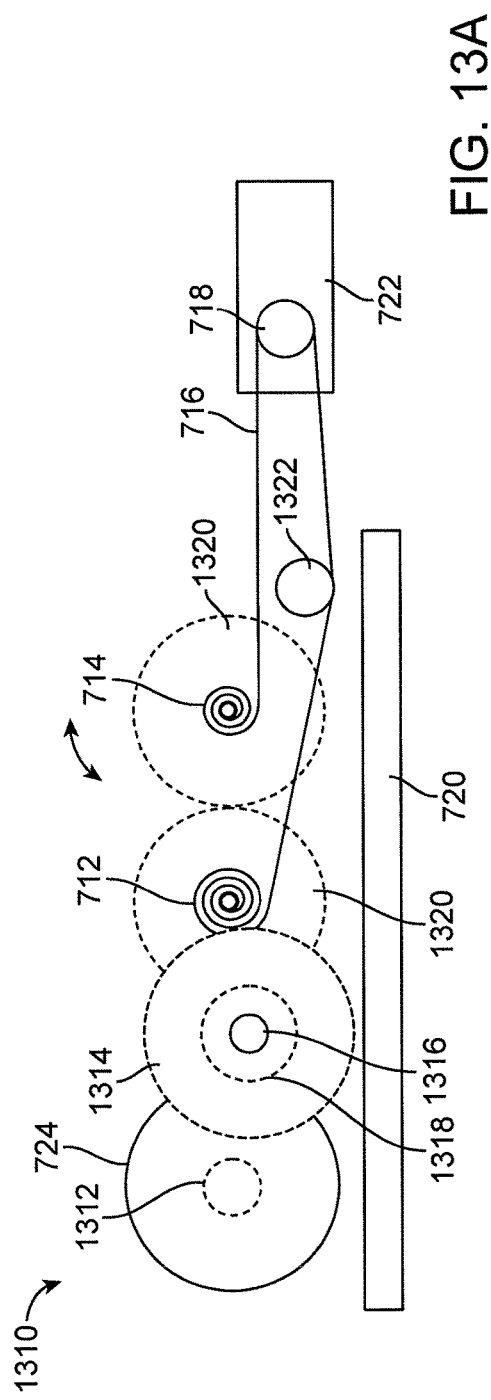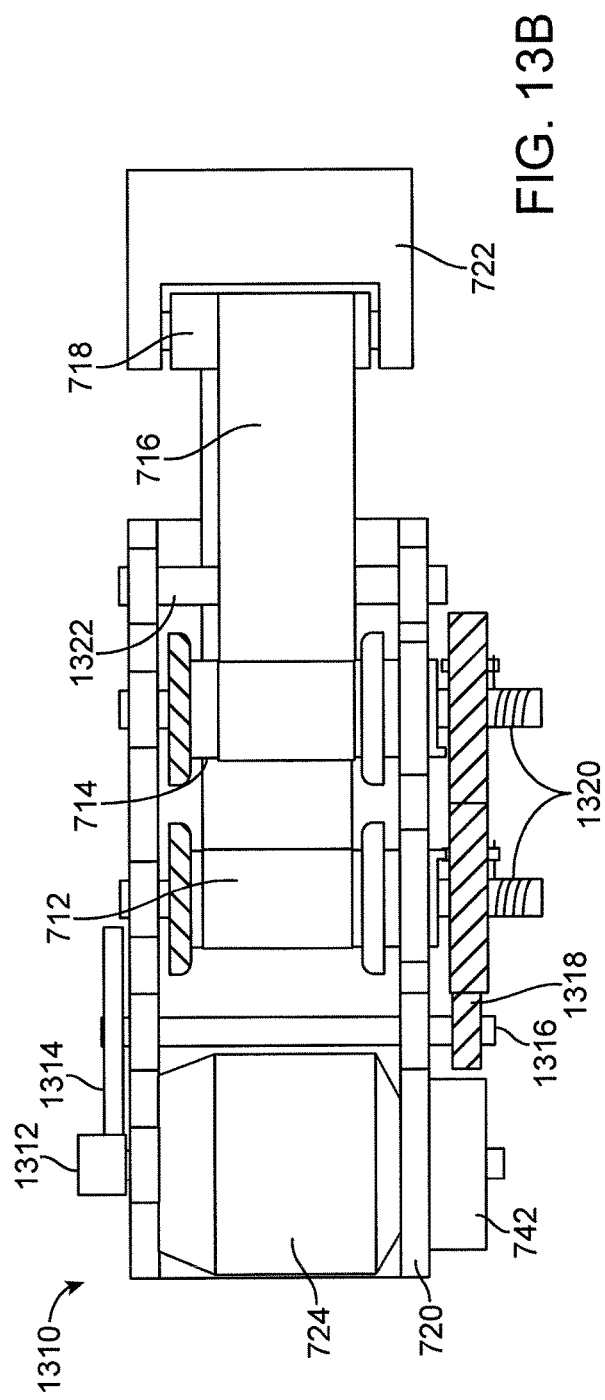
FIG. 13A
FIG. 13B

ORTHOTIC DEVICE DRIVE SYSTEM AND METHOD

CROSS REFERENCE TO RELATED APPLICATIONS

This application claims priority to U.S. Provisional Application No. 61/798,101 titled "Orthotic Device Drive System and Method," and filed Mar. 15, 2013, the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the present invention relate generally to orthotics, and more specifically to drive systems, components and methods for active orthotics.

BACKGROUND

Wearable active orthotic devices can be used to amplify the residual intention to extend or flex a joint of patients recovering from neuromuscular deficiencies arising from conditions including stroke, traumatic brain injury and multiple sclerosis, or patients recovering from complex orthopedic injuries. Such orthotic devices can be attached across various joints to which movement assistance is provided, such as across a knee, elbow or ankle. The active orthotic device typically has a first portion that attaches to the patient on one side of the joint, a second portion that attaches on the other side of the joint, and an actuator that movably couples the first and second orthotic portions to provide force(s) to assist with movement of the joint. For example, in a knee augmentation device, the first portion is attached around the thigh and the second portion is attached around the calf. The intention to extend the joint may be sensed by a foot pressure sensor.

Considerable force may be required when assisting a joint such as the knee or elbow. The requirements for the actuator are difficult to provide in a compact, lightweight, battery-operated, wearable device.

Many assistive devices use actuators in which a motor is coupled to a lead screw, which may be an Acme screw or ball screw. The lead screw provides both a rotary to linear motion transformation as well as a gear reduction. It may take 10's of rotations of the ball screw to flex the joint less than 180 degrees, thereby providing an effective gear ration that may typically fall in the range of 20:1 to 100:1. The total ratio to the motor may be further increased by using a gear reduction or pulley coupling with different diameter pulleys. The use of a ball screw can meet the basic requirements, but has several disadvantages. The stroke of a ball screw is determined by the length of the screw and the size of the actuator cannot be reduced beyond the length necessary to supply the stroke required to link with the orthotic device. If the linkage is changed to provide the same range of motion with a shorter stroke, the force of the linear actuator must be increased and that may exceed the strength of the screw or available torque of the driving motor.

Other actuators have a difficult time meeting the output torque requirements while keeping size and weight low. If the actuator uses direct gearing, such as planetary gears, spur gears, or harmonic drive, the final gear must supply the entire torque and requires a large, heavy gear. Direct gearing also does not have a mode in which the drive mechanism is completely decoupled from the output linkage. Such decoupling is highly desirable for rehabilitation robotics in which the patient should be allowed free swing of the leg or arm in between the times when the powered assistance lifts, supports and/or assists the patient. Further, direct drive has a single gear ratio. In powered assistance of the knee, smaller motors can be used if the drive mechanism has different drive ratios to accommodate the need for high torque (for sit-to-stand or stair ascent) when the knee is bent near 90 degrees, and to provide higher speed (with less torque) for fast walking when the knee is nearly straight.

What would be desirable, but is not provided by the prior art, is an actuator that obtains high force without ball screws or large output gears, allows free movement of a patient when no movement assistance is desired, and varies the drive ratio during the stroke.

SUMMARY OF THE DISCLOSURE

The present invention relates to orthotics, and more specifically to drive systems, components, and methods for active orthotics.

In some embodiments, an active assistance orthosis is provided with a first portion configured to attach to a patient on one side of a joint, a second portion configured to attach to the patient on an opposite side of the joint, and an actuator configured to apply a force between the first and the second portions of the orthosis. In some embodiments, the actuator comprises a first spool rotatably mounted to the first portion, a second spool also rotatably mounted to the first portion, an output pulley mounted to the second portion, and a belt. The belt may have a first end wrapped around the first spool, a second end wrapped around the second spool, and a mid-portion wrapped around the output pulley. The actuator in these embodiments is configured to pull the output pulley toward the first portion when the first spool is rotated to pull the belt a given length and the second spool is rotated to feed the belt less than the given length.

In some of the above embodiments, the second spool is configured to feed the belt less than the given length pulled by the first spool due to a diameter of belt turns on the first spool exceeding a diameter of belt turns on the second spool. The first spool and the second spool may be configured to rotate at a same speed. The first spool and the second spool may be configured to rotate in the same direction or in opposite directions.

The actuator may include a belt tensioner configured to take up slack in the belt. This belt tensioner may include a rotatable drum separate from the first spool, the second spool and the output pulley. In some embodiments, the rotatable drum includes at least one moving roller configured to interact with at least one fixed roller to increase a belt path length. The belt tensioner may include a rotational position sensor coupled to the rotatable drum. In some embodiments, the sensor is configured to communicate with a controller to indicate a belt tension when there is no slack in the belt.

In some embodiments, the orthosis may include a belt having a thickness no greater than about 0.005 inches. In some embodiments, the orthosis may include a polycentric hinge coupling the first portion to the second portion. In these embodiments, the orthosis may include a bell crank linkage coupling the first portion to the second portion, and the output pulley may be located on the bell crank linkage.

In some embodiments, the orthosis may include an actuator configured to provide a winch ratio between the first spool and an angle of the orthosis, wherein the winch ratio is higher when the orthosis is bent (near 90°) than when it is straight. In these embodiments, the actuator may be configured to provide a first winch ratio when the orthosis is positioned at about a 90° angle and a second winch ratio when the orthosis is positioned at about a 0° angle. The first winch ratio may be configured to be at least twice the second winch ratio. In some embodiments, the first winch ratio may be configured to be about four times or more greater than the second winch ratio.

Methods of assisting movement of a patient are also provided. In some embodiments, the method includes attaching a first portion of an orthosis to a patient on one side of a joint, attaching a second portion of an orthosis to the patient on an opposite side of the joint, and detecting a residual intention of the patient to move the joint. The patient is assisted with the intended movement by applying an assistive force to the patient with an actuator applying a force between the first and the second portions of the orthosis. In some embodiments, the actuator comprises a first spool rotatably mounted to the first portion, a second spool also rotatably mounted to the first portion, an output pulley mounted to the second portion, and a belt. The belt may have a first end wrapped around the first spool, a second end wrapped around the second spool, and a mid-portion wrapped around the output pulley.

In some embodiments, the assisting step of the method includes rotating the first spool to pull the belt a given length, and rotating the second spool to feed the belt less than the given length such that the output pulley on the second portion is pulled towards the first portion of the orthosis.

In some embodiments, the attaching a first portion step includes attaching the first portion of the orthosis around a thigh of the patient, and the attaching a second portion step includes attaching the second portion around a calf of the patient. In other embodiments, the attaching a first portion step includes attaching the first portion of the orthosis around an upper arm of the patient, and the attaching a second portion step includes attaching the second portion around a lower arm of the patient.

In general, in one embodiment, a harmonic winch includes a first spool rotatably mounted to a first housing. A second spool is rotatably mounted to the first housing. An output pulley is mounted to the second housing. A belt has a first end wrapped around the first spool, a second end wrapped around the second spool, and a mid-portion wrapped around the output pulley. A motor is configured to rotate the first spool and the second spool. The rotation of the first spool pulls the belt a given length and the rotation of the second spool feeds the belt less than the given length so as to pull the output pulley and the second housing towards the first housing.

In general, in one embodiment, an active assistance orthosis includes a first portion configured to attach to a patient on one side of a joint. A second portion is configured to attach to the patient on an opposite side of the joint. An actuator is configured to apply a force between the first and the second portions of the orthosis. The actuator includes a first spool rotatably mounted to the first portion. A second spool is rotatably mounted to the first portion. An output pulley is mounted to the second portion. A belt has a first end wrapped around the first spool, a second end wrapped around the second spool, and a mid-portion wrapped around the output pulley. The actuator is configured to rotate the first spool and the second spool. The rotation of the first spool pulls the belt a given length and the rotation of the second spool feeds the belt less than the given length so as to pull the output pulley towards the first portion. Pulling the output pulley towards the first portion pulls at least part of the second portion towards at least part of the first portion.

Any of these embodiments can include one or more of the following features. The second spool can be configured to feed the belt less than the given length pulled by the first spool due to a diameter of belt turns on the first spool exceeding a diameter of belt turns on the second spool. The first spool and the second spool can be configured to rotate at a same speed. The first spool and the second spool can be configured to rotate in a same direction. The first spool and the second spool can be configured to rotate in opposite directions. The actuator can further include a belt tensioner configured to take up slack in the belt. The belt tensioner can include a rotatable drum separate from the first spool, the second spool, and the output pulley. The rotatable drum can include at least one moving roller configured to interact with at least one fixed roller to increase a belt path length. The belt tensioner can include a rotational position sensor coupled to the rotatable drum, and the sensor can be configured to communicate with a controller to indicate a belt tension when there is no slack in the belt. The belt can have a thickness no greater than about 0.005 inches.

Any of these embodiments can include one or more of the following features. The orthosis can further include a polycentric hinge coupling the first portion to the second portion. The orthosis can further include a bell crank linkage coupling the first portion to the second portion, and the output pulley can be located on the bell crank linkage. The actuator can be configured to provide a winch ratio between the first spool rotation and the orthosis hinge rotation. The winch ratio can be higher when the orthosis is bent than when it is straight. The actuator can be configured to provide a first winch ratio when the orthosis is positioned at about a 90° angle and a second winch ratio when the orthosis is positioned at about a 0° angle. The first winch ratio can be more than twice the second winch ratio. The orthosis can further include a hinge coupling the first portion to the second portion. Pulling at least part of the second portion towards at least part of the first portion can include rotating the first portion relative to the second portion about the hinge. The actuator can be configured to apply a lower torque and higher speed as the hinge angle between the first portion and the second portion decreases.

Any of these embodiments can include one or more of the following features. The orthosis can further include a motor configured to drive rotation of the first spool and the second spool, a drive sprocket connected to the motor, and a driven sprocket connected to the first spool. The drive sprocket and the driven sprocket can be connected by a second belt. The driven sprocket can have a larger diameter than the drive sprocket.

Any of these embodiments can include one or more of the following features. Rotating the first spool and the second spool to pull at least part of the second portion towards at least part of the first portion can include rotating the first spool and the second spool in a first direction. The actuator can be further configured to rotate the first spool and the second spool in a second direction to allow the output pulley to move away from the first portion so as allow the at least part of the second portion to move away from the at least part of the first portion. The first portion can be configured to attach above the patient's knee and the second portion can be configured to attach below the patient's knee. The orthosis can further include a rotational position sensor coupled to the actuator. The rotational position sensor can be configured to communicate with a controller to indicate a position of the first portion relative to the second portion. The orthosis can further include a belt tensioner, tensioner position sensor, and spool rotation counter, and the rotational position of the first portion relative to the second portion can be determined by a controller based on the spool rotation counter and belt tensioner position.

In general, in one embodiment, a method of assisting movement of a patient includes (1) attaching a first portion of an orthosis to a patient on one side of a joint; (2) attaching a second portion of the orthosis to the patient on an opposite side of the joint; (3) detecting a residual intention of the patient to move the joint; and (4) assisting the patient with the intended movement by applying an assistive force to the patient with an actuator. The actuator includes a first spool rotatably mounted to the first portion, a second spool also rotatably mounted to the first portion, and an output pulley mounted to the second portion. The actuator further includes a belt having a first end wrapped around the first spool, a second end wrapped around the second spool, and a mid-portion wrapped around the output pulley.

Any of these embodiments can include one or more of the following features. The assisting step can include rotating the first spool to pull the belt a given length and rotating the second spool to feed the belt less than the given length such that the output pulley on the second portion is pulled towards the first portion of the orthosis. Attaching a first portion can include attaching the first portion of the orthosis around a thigh of the patient, and attaching a second portion can include attaching the second portion around a calf of the patient. Attaching a first portion can include attaching the first portion of the orthosis around an upper arm of the patient, and attaching a second portion step can include attaching the second portion around a lower arm of the patient.

The actuator or winch can be used to provide assistance during extension of a joint while allowing unassisted movement during flexion of the joint. The spools can be rotated to a position where there is slack in the belt to allow unassisted movement of the joint.

In addition to use in active orthotic devices as detailed herein, the compact high-force actuator systems, components and methods of this disclosure are useful in a variety of other applications as well. These applications may include, but are not limited to, patient lifts, rehabilitation equipment, exercise equipment, and mechanical devices for lifting, hauling and positioning.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7A is a side elevation view of an exemplary harmonic winch actuator. FIG. 7B is a top plan view of the actuator shown in FIG. 7A.

FIG. 13A is a side elevation view showing another exemplary embodiment of a harmonic winch actuator.

FIG. 13B is a top plan view showing the actuator of FIG. 13A.

DETAILED DESCRIPTION

General Overview of a Knee Orthosis

Figure 1:
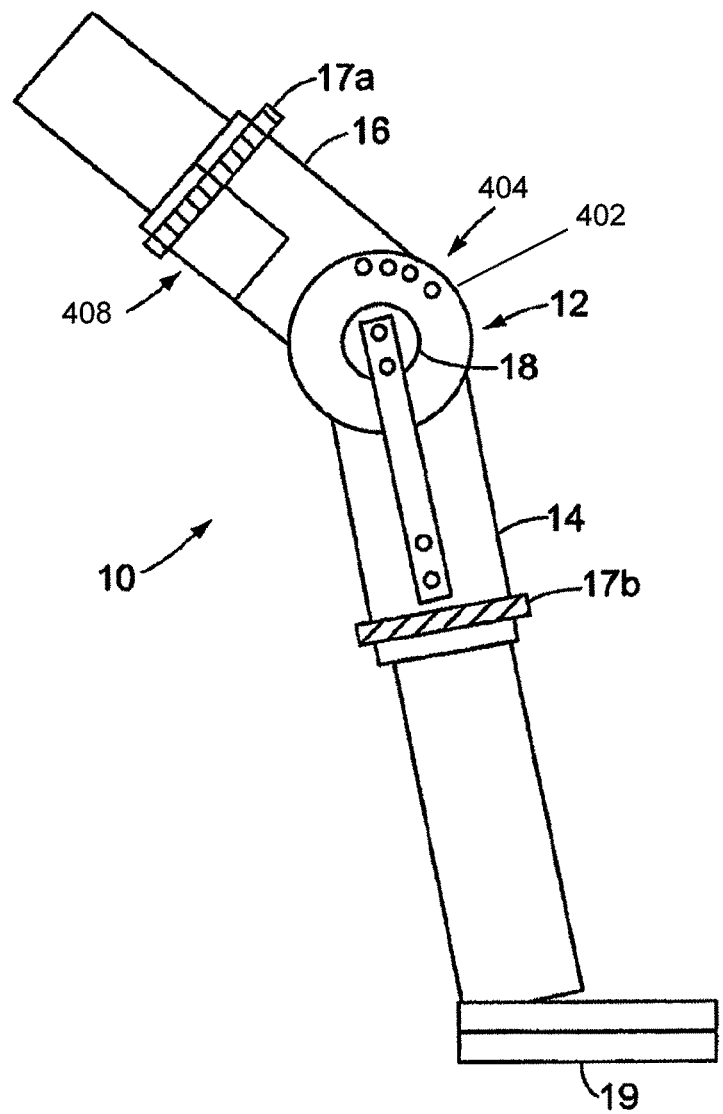
FIG. 1 shows an active knee orthosis.

FIG. 1 schematically shows an exemplary active muscle support orthosis according to one embodiment of the invention. The device 10 is an active knee orthosis or brace used to offload some of the stress from the quadriceps when extending or flexing the leg. For different parts of the body, other devices are constructed with a suitable shape, but the principles presented here apply by analogy to such devices. The device 10 is particularly useful in helping someone with muscle weakness in the everyday tasks of standing, sitting, walking, climbing stairs, and descending stairs. The device 10 includes an upper portion 16 configured to be placed around the user's upper legs (such as the thighs), a lower portion 14 configured to be placed around the user's lower legs (such as the calf), and an actuator 12 therebetween. The support to the muscle is defined by the position of the actuator 12 applying force to the moving parts of the orthosis 10. Namely, as the actuator 12 rotates, and with it the moving (rigid) parts of the orthosis, the position of the actuator 12 defines the relative position of the joint and thereby supports the corresponding muscle. The actuator 12 can be used principally to provide assistance during extension of a joint. As described further below, the actuator 12 can be a harmonic winch actuator that advantageously provides high torque, varies the drive or winch ratio during the stroke, and provides for free movement of the joint when assistance is not desired.

The device 10 can provide assistance and/or resistance to the muscles that extend and flex a joint. In some embodiments, resistance can be provided to resist the force exerted by the muscles, and/or resistance can also be provided to resist or oppose the force of gravity. The device 10 can be configured so as to not directly connect to the muscle, but rather be attached in such a way that it can exert external forces to the limbs.

The device 10 can be built from an underlying structural frame (such as of lightweight aluminum or carbon fiber), padding, and straps (not shown) that can be tightened to the desired pressure. The structural frame of the device 10 includes a rigid upper portion 16 above the knee connected to a hinge 18 at the medial and lateral sides. The upper portion 16 can extend up to the mid-thigh. The structural frame 10 further includes a rigid lower portion 14 below the knee that extends from the hinge 18 down to the mid-calf. In the thigh and calf regions, the frame extends around from medial to lateral sides around approximately half the circumference of the leg. The remaining portion of the circumference is spanned by straps that can be tightened with clips, laces, hook and loop closures (such as Velcro®), clip-type connectors 17, and/or by a zipper type fastener. Understandably, this allows easier attachment and removal of the device. The rigid portions 14, 16 can be either on the anterior or posterior side. The number and width of straps can vary, but the straps must be sufficient to hold the device in place with the axis of rotation of the hinge in approximately the same axis as that of rotation of the knee. The hinge 18 itself may be more complex than a single pivot point to match the rotation of the knee. In more general terms, in some embodiments, the device 10 has a frame that has a first structural portion that is attached to the body above or proximally the joint, a second structural portion that is attached to the body below or distally to the joint, and an articulating joint portion connecting the first structural portion with the second structural portion.

Cushioning material may be added to the device 10 to improve comfort. In some embodiments, a manufacturer may choose to produce several standard sizes of the device 10, each with enough adjustments to be comfortable for a range of patients. In other embodiments, the manufacturer may use a mold or tracing of the leg to produce individually customized devices 10. In still other embodiments, a single size of the device 10 may be produced that may be adjusted to fit a wide variety of patients.

A microcontroller-based control system can drive control information to the actuator (such as the winch actuator described below), receive user input from a control panel function, and receive sensor information including joint position and external applied forces. For example, pressure information is obtained from the foot-pressure sensor 19. Based on the sensor input and desired operation mode, the control system can apply forces to resist the muscle, apply force to assist the muscle, or allow the muscle to move the joint freely.

Figure 2:
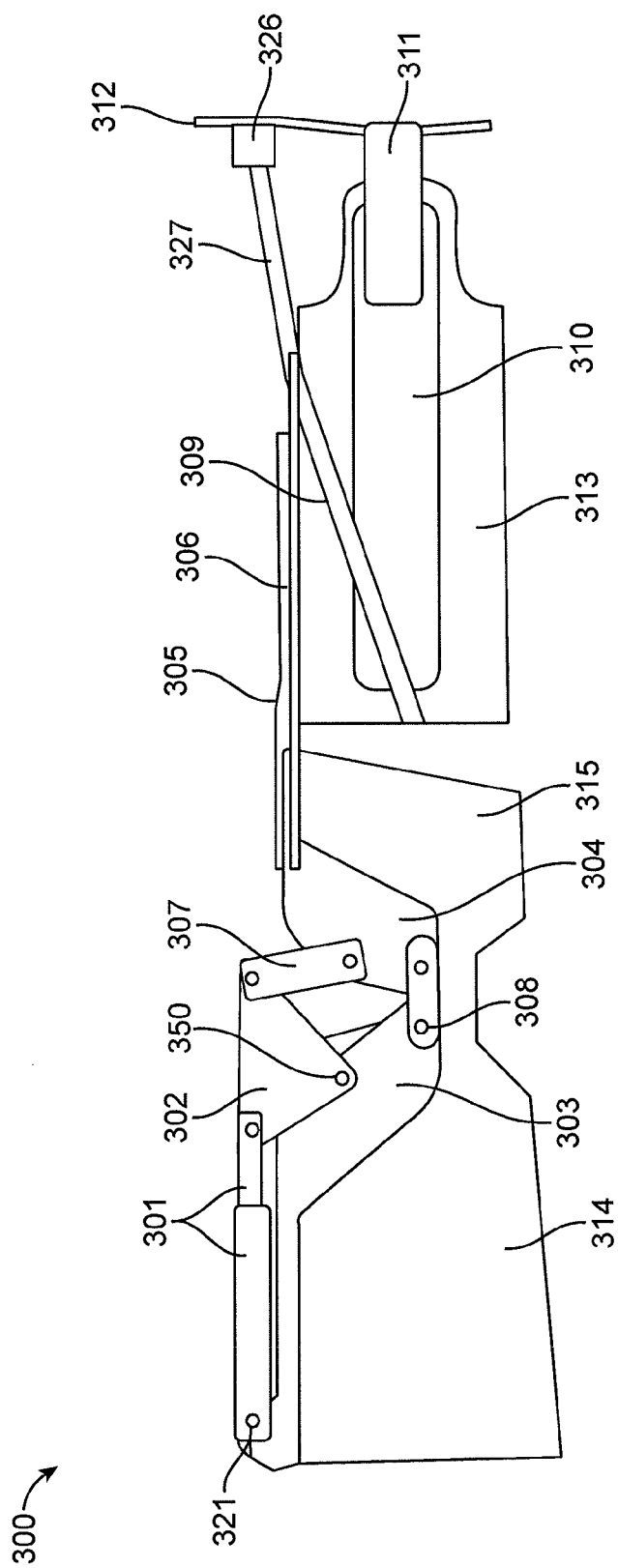
FIG. 2 illustrates a mechanical linkage between an actuator and the body attachment of an orthosis.

FIG. 2 illustrates a side-view diagram of an orthotic system according to an exemplary embodiment of the invention. In the illustrated embodiment, orthotic system 300 includes: linear actuator 301 (which may be replaced by the harmonic winch actuator described further below); bell crank 302; thigh orthotic structure 303; lower leg orthotic structure 304; tibia anterior structure 305; tibia posterior structure 306; connector link 307; hinge 308; tibia suspension system 309; lateral support structures 310; ankle suspension structure 311; footpad sensor system 312; lower leg textiles 313; thigh textile 314; upper shin textile 315; toe strap 326; and anti-foot drop system 327. However, this is given by way of example and not limitation, as the orthotic system described herein may include fewer or more components. The linear actuator 301 acts directly on a linkage point of a bell crank rocker arm 302. Further, the linear actuator 301 is mounted on a pivot 321 at the upper most end of the thigh orthotic structure 303. However, other embodiments can include the linear actuator 301 being constrained on a fixed plane or fixed via pivot on any portion of the thigh orthotic structure 303 or lower leg orthotic structure 304 or other structural parts. Alternate embodiments can also include indirect actuation via an input link between the linear actuator 301 and the bell crank 302.

Figure 3:
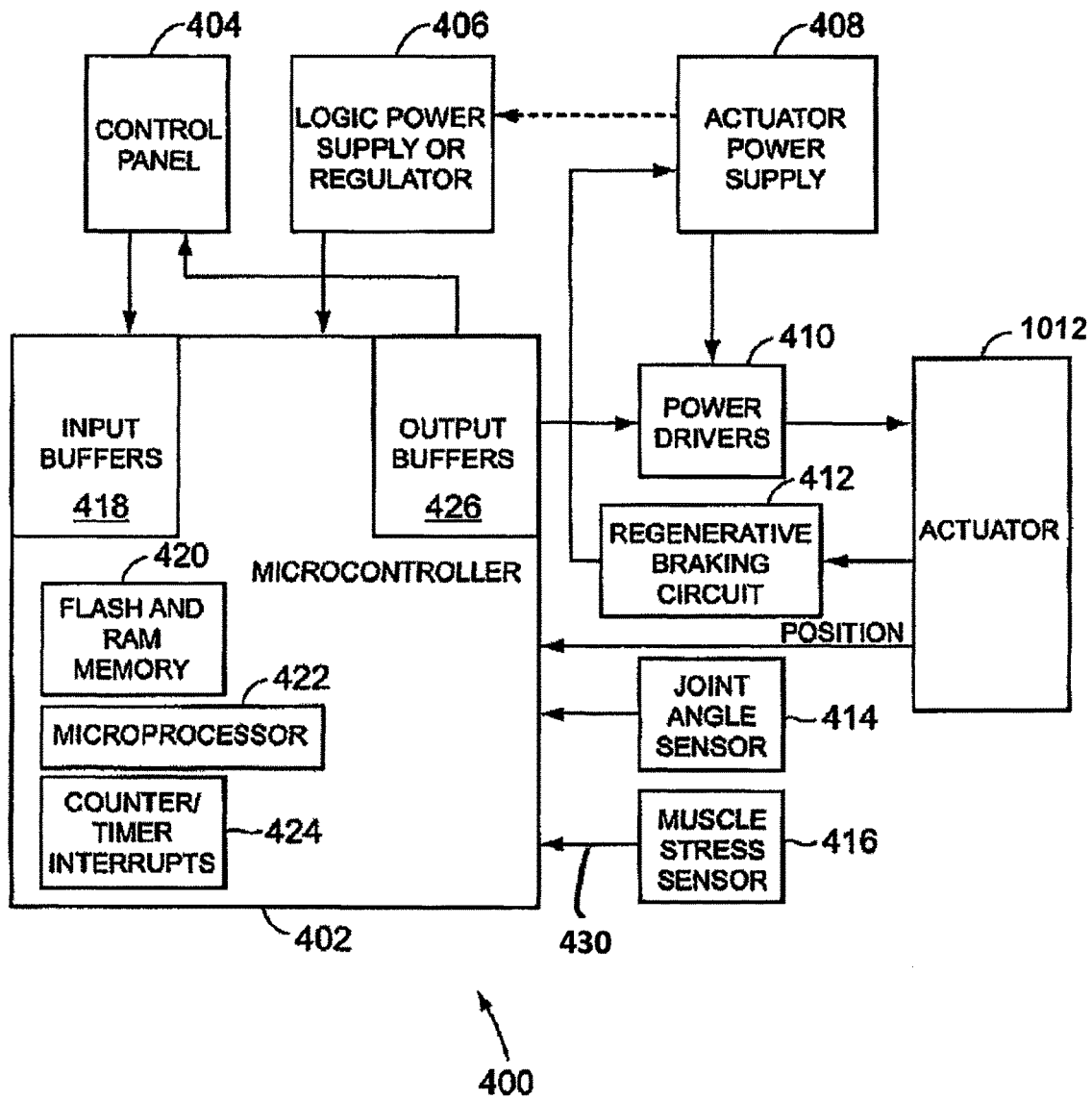
FIG. 3 is a block diagram showing the electronics used to drive and control an active muscle assistance device.

FIG. 3 is a block diagram showing an exemplary electronics and control system for an orthosis as described herein. The operation of the device may be controlled by a program running in a microcontroller 402. To minimize the physical size of the control system, the microcontroller may be selected based on the scope of its internal functionality.

In the exemplary embodiment of FIG. 3, the microcontroller 402 is coupled to a control panel 404 to provide user control and information on the desired mode of operation. The control panel includes a set of switches that can be read through the input buffers 418 of the microcontroller. The control panel also may have a display panel or lights to display information, such as operational mode and battery state. The control panel also includes means to adjust the strength of assistance and resistance in order to customize the forces to the ability of the user. Another embodiment of the control panel is a wired or wireless connection port to a handheld, laptop or desktop computer. The connection port can also be used to communicate diagnostic information and previously stored performance information.

The control panel may be part of the actuator or may be attached to another part of the structural frame with wires connected to the actuator. In some embodiments, buttons of the control panel can be of the type that can be operated through clothing to allow the device mode to be changed when the device is hidden under the clothes. In other embodiments, the device can be worn on top of clothing or can be worn directly on the skin and remain uncovered.

Outputs of the microcontroller, provided from the output buffers 426, can be directed in part to the actuator 1012 (such as the winch actuator described below) through a power driver circuit 410 and in part to the control panel 404. In one embodiment, the driver circuit converts the outputs to high voltage phases to drive an electrostatic actuator. The power driver circuit includes transformers and rectifiers to step up a-c waveforms generated by the microcontroller. In instances where the actuator is a DC motor, servomotor, or gear motor, the power driver circuit may be designed to generate high-current multi-phase signals.

When the operation mode of the muscle assistance device is set to apply a force that opposes the motion of the joint, the energy input from that 'external' force must be absorbed by the control circuit. While this energy can be dissipated as heat in a resistive element, it may also be returned to the battery in the actuator power supply 408 via a regeneration braking circuit 412. This concept is similar to "regenerative braking" found in some types of electric and hybrid vehicles to extend the operation time before the battery needs to be recharged.

In some embodiments, the microcontroller 402 can receive digital information via a digital interface connection 430 from a muscle stress sensor 416 that includes an analog to digital converter. In other embodiments, the analog to digital converter can be located in the microcontroller 402 and the muscle stress sensor 416 can output analog data. The joint angle sensor 414 provides the joint angle via a belt position sensor, potentiometer or optical sensor of a type known in the art, or by an encoder coupled to a lead screw or other drive component.

When the orthotic device is used to assist leg extension, the muscle stress sensor 416 may be implemented as a foot-pressure sensor (such as pressure sensor 19 in FIG. 1) wired to the active orthosis. In one embodiment, this sensor is implemented with parallel plates separated by a dielectric that changes total capacitance under pressure. The foot sensor may be a plastic sheet with conductive plates on both sides so that when pressure is applied on the knee the dielectric between the plates compresses. The change in the dielectric changes the capacitance and that capacitance change can be signaled to the microcomputer indicating to it how much pressure there is on the foot. Other pressure sensors may use resistive ink that changes resistance when pressure is applied on it. Yet another type of pressure sensor, such as a strain gauge can be alternatively used to supply the pressure information. Further sensor constructs are subsequently described in more detail. These sensors are configured to detect the need or intention to exert a muscle. For example, the foot pressure sensor in conjunction with joint angle sensor detects the need to exert the quadriceps to keep the knee from buckling. Other types of sensors, such as strain gauges, can detect the intention by measuring the expansion of the leg circumference near the quadriceps. In another embodiment, surface mounted electrodes and signal processing electronics measure the myoelectric signals controlling the quadriceps muscle. When the orthotic device is used for other muscle groups in the body, appropriate sensors can be used to detect either the need or intention to flex or extend the joint being assisted. It is noted that there may be a certain threshold (minimum amount of force), say 5 pounds on the foot, above which movement of the actuator is triggered.

Power for the muscle assistance devices described herein can come from one or more battery sources feeding power regulation circuits. The power for the logic and electronics is derived from the primary battery (in the power supply 408). The battery-charge state is fed to the microcontroller for battery charge status display or for activating low battery alarms. Such alarms can be audible, visible, or a vibration mode of the actuator itself. Alternatively, a separate battery can power the electronics portion.

Figure 4:
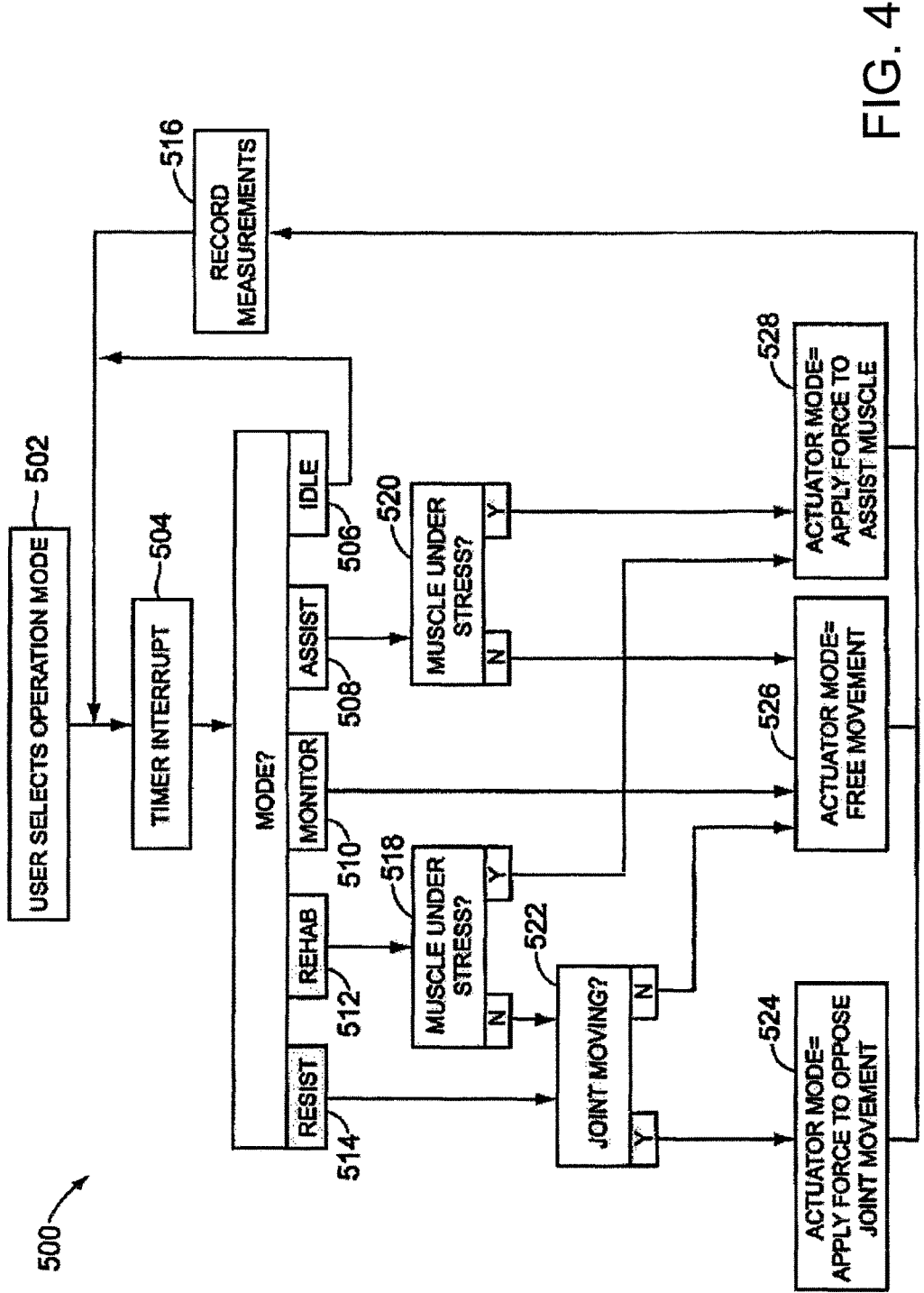
FIG. 4 is flowchart showing the modes of operation of a muscle assistance device.

Turning now to FIG. 4, the operation of an exemplary muscle assistance device is illustrated with a block diagram. The algorithm in this diagram is implemented by embedded program code executing in the microcontroller. In the first step of FIG. 4, the user selects a mode of operation 502. The modes include: idle 506, assist 508, monitor 510, rehabilitate 512, and resist 514.

In the idle mode 506, the actuator is set to neither impede nor assist movement of the joint. This is a key mode in some implementations because it allows the device to move freely or remain in place when the user does not require assistance or resistance, or if battery has been drained to the point where the device can no longer operate. In idle mode, the actuator allows free movement with a clutch or an inherent free movement mode of the actuator, for example, even when primary power is not available.

In the monitor mode 510, the actuator is in free movement mode (not driven), but the electronics are activated to record information for later analysis. Measured parameters include a sampling of inputs from the sensors and counts of movement repetitions in each activation mode. This data may be used later by physical therapists or physicians to monitor and alter rehabilitation programs.

In the assist mode 508, the actuator is programmed to assist movements initiated by the muscle. This mode augments the muscle, supplying extra strength and stamina to the user. In the assist mode 508, the device can also resist the force exerted by gravity. This use of the term "resist" is not to be confused with the way the term "resist" is used in the description of the resist mode 514, as described below. Again, as mentioned herein with respect to FIGS. 4 and 5, "resist" can refer to both resisting gravity as described in the assist mode and to resisting the force exerted by muscle as described below in the resist mode.

In the resist mode 514, the device is operating as an exercise device. Any attempted movement is resisted by the actuator. Resistance intensity controls on the control panel determine the amount of added resistance. In the resist mode 514, the device resists the force exerted by the muscle.

In the rehabilitate mode 512, the device provides a combination of assistance and resistance in order to speed recovery or muscle strength while minimizing the chance of injury. Assistance is provided whenever the joint is under severe external stress, and resistance is provided whenever there is movement while the muscle is under little stress. This mode levels out the muscle usage by reducing the maximum muscle force and increasing the minimum muscle force while moving. The average can be set to give a net increase in muscle exertion to promote strength training. A front panel control can provide the means for setting the amplitude of the assistance and resistance.

Then, assuming that the rehabilitate mode 510 is selected, a determination is made as to whether the muscle is under stress. The indicia of a muscle under stress is provided as the output of the muscle stress sensor reaching a predetermined minimum threshold. That threshold is set by the microcontroller in response to front panel functions.

If the muscle is not under stress or if the resist mode 514 is selected, a further determination is made as to whether the joint is moving 522. The output of the joint position sensor, together with its previous values, indicates whether the joint is currently in motion. If it is, and the mode is either rehabilitate or resist, the actuator is driven to apply force opposing the joint movement 524. The amount of resistance is set by the microcontroller in response to front panel settings. The resistance may be non-uniform with respect to joint position. The resistance may be customized to provide optimal training for a particular individual or for a class of rehabilitation.

If the joint is not in motion 522 or the monitor mode 510 is selected, the actuator is de-energized to allow free movement of the joint 526. This may be accomplished by using an actuator that has an unpowered clutch mode.

Additionally, if the muscle is under stress 520 or 522 and either the rehabilitate or the assist modes are selected, the actuator is energized to apply force for assisting the muscle 528. The actuator force directed to reduce the muscle stress. The amount of assistance may depend on the amount of muscle stress, the joint angle, and the front panel input from the user. Typically, when there is stress on the muscle and the joint is flexed at a sharp angle, the largest assistance is required. In the case of knee assistance, this situation would be encountered when rising from a chair or other stressful activities.

As mentioned before, when the device is in monitor mode 510, measurements are recorded to a non-volatile memory such as the flash memory of the microcontroller (item 420 in FIG. 3). Measurements may include the state of all sensors, count of number of steps, time of each use, user panel settings, and battery condition. This and the step of uploading and analyzing the stored information are not shown in the diagram.

Figure 5:
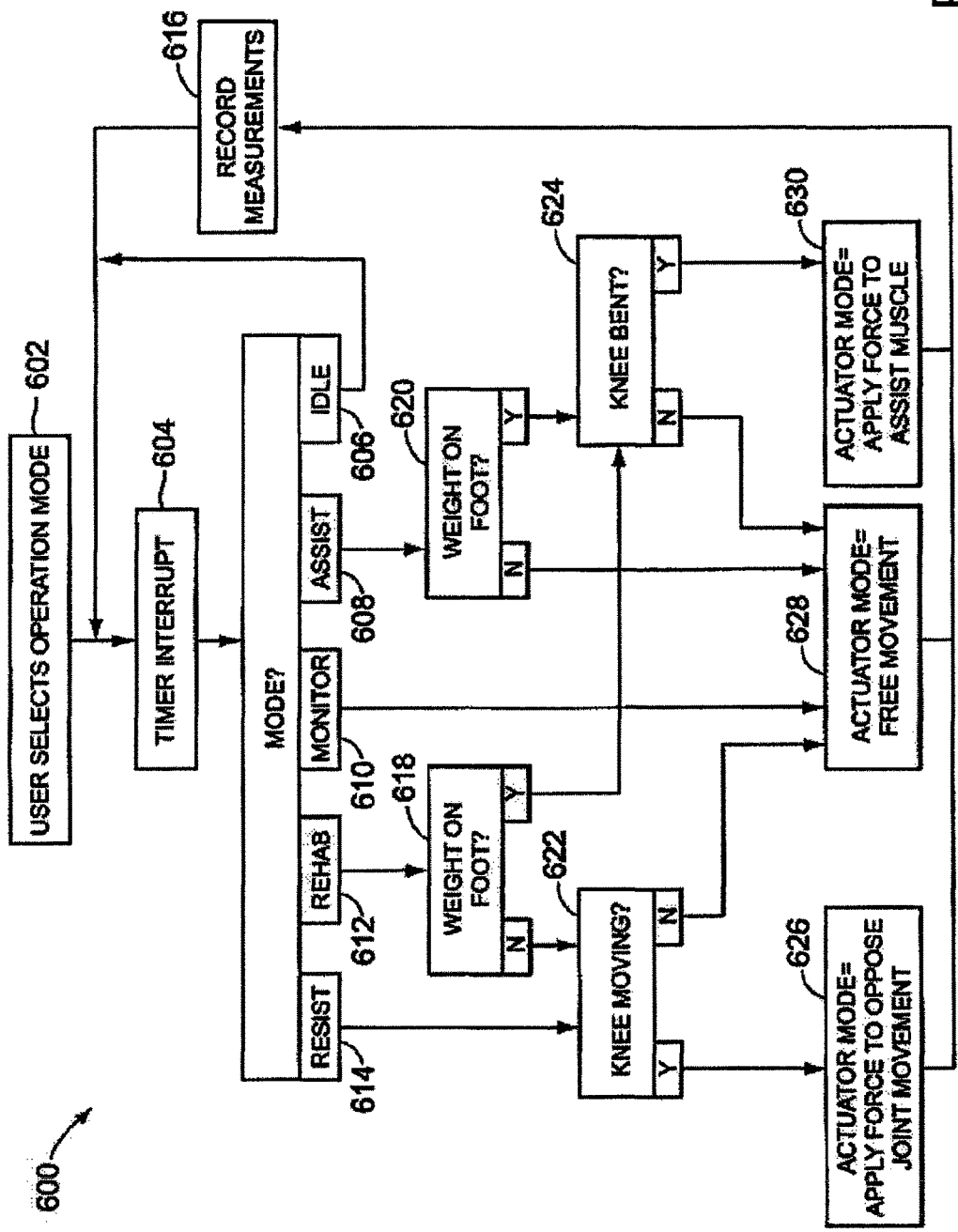
FIG. 5 is a flowchart of the modes of operation of a knee joint muscle assistance device.

FIG. 5 is a flow diagram specific to an active knee assistance device. This diagram assumes a specific type of muscle stress sensor that measures the weight on the foot. Relative to the diagram of FIG. 5, this diagram also shows a step (620) to determine whether the knee is bent or straight (within some variation). If the knee is straight, no bending force is needed 624 and power can be saved by putting the actuator in free-movement mode 630. To prevent problems such as buckling of the knee, the transitions, i.e., de-energizing the actuator, in both FIGS. 5 and 6 may be dampened to assure that they are smooth and continuous.

The software running on the microcontroller may be architected in many different ways. One architecture is to structure the embedded program code into subroutines or modules that communicate with each other and receive external interrupts (see item 424 in FIG. 3). Other embodiments are not interrupt driven. In one implementation the primary modules include control panel, data acquisition, supervisor, actuator control, and monitor modules. A brief description of these modules is outlined below.

The control panel responds to changes in switch settings or remote communications to change the mode of operation. Settings may be saved in a nonvolatile memory, such as a bank of flash memory.

The data acquisition module reads the sensors and processes data into a format useful to the supervisor. For instance, reading position from a capacitive position sensor involves reading the current voltage, driving a new voltage through a resistance, then determining the RC time constant by reading back the capacitor voltage at a later time.

The supervisor module may be a state machine for keeping track of high-level mode of operation, joint angle, and movement direction. States are changed based on user input and sensor position information. The desired torque, direction and speed to the actuator control the functioning of this module. The supervisor module may also include training, assistance, or rehabilitation profiles customized to the individual.

The actuator control module is operative to control the actuator (low level control) and includes a control loop to read fine position of the actuator and then drive phases to move the actuator in the desired direction with requested speed and torque. The monitor module monitors the battery voltage and other parameters such as position, repetition rates, and sensor values. It also logs parameters for later analysis and generates alarms for parameters out of range. This module uses the front panel or vibration of the actuator to warn of low voltage from the battery.

A number of variations in the above described system and method include, for example, variations in the power sources, microcontroller functionality, and the like. Specifically, power sources such as super capacitors, organic batteries, disposable batteries and different types of rechargeable batteries can be used in place of a regular rechargeable battery. Moreover, microcontroller functionality can be split among several processors or a different mix of internal and external functions. Also, different types of orthotic devices, with or without hinges and support frames, may be used for attachment to the body, and they may be of different lengths. Various ways of communicating the 'weight-on-foot' may be used, either through wired or wireless connections to the control circuitry, or by making the orthosis long enough to reach the foot.

Harmonic Winch Actuator

Figure 6A:
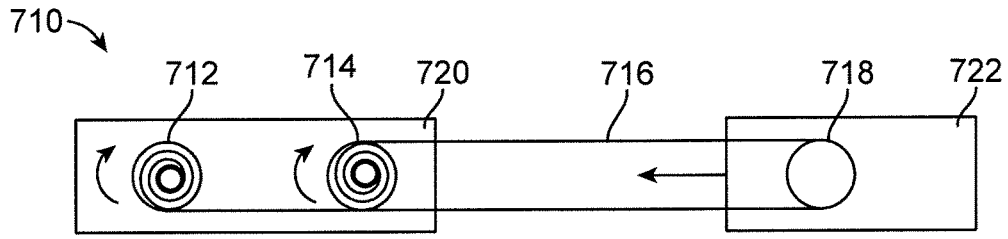
FIG. 6A is a side view of an exemplary harmonic winch actuator shown at the beginning of its stroke.
Figure 6B:
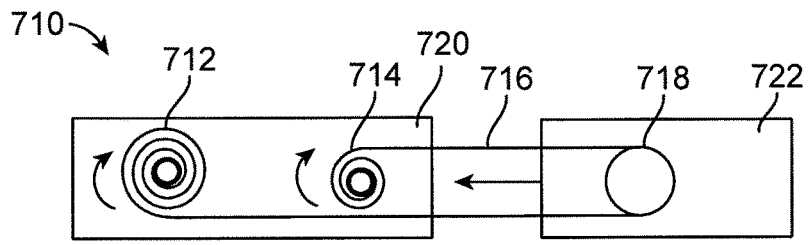
FIG. 6B is a side view of the actuator of FIG. 6A shown at the end of its stroke.

Referring to FIGS. 6A-17B, various exemplary embodiments of harmonic winch actuators will now be described. FIGS. 6A-6D highlight basic concepts of construction and operation of some of these embodiments. Referring first to FIGS. 6A and 6B, a first embodiment is schematically shown. FIG. 6A shows harmonic winch actuator 710 at the beginning of its stroke and FIG. 6B shows winch actuator 710 at the end of its stroke. Winch actuator 710 includes a first spool 712, a second spool 714, and a belt 716 coupled between the two spools 712, 714. Belt 716 has a first end attached to first spool 712, a second end attached to second spool 714, and a mid-portion that loops around a pulley 718. First spool 712 and second spool 714 are rotatably mounted to first housing 720, and pulley 718 is rotatably mounted to second housing 722. In operation, winch actuator 710 moves second housing 722 with respect to first housing 720. For example, first housing 720 may be located on an upper portion of a knee orthosis and second housing 722 may be located on a lower portion of the knee orthosis, such that winch actuator 710 is able to drive (e.g., rotate) the lower portion of the orthosis relative to the upper portion.

When winch actuator 710 is at the beginning of its stroke as shown in FIG. 6A, roughly equal amounts of belt 716 are wound around first spool 712 and second spool 714. In this mode, first spool 712 operates as a pull spool, and second spool 714 operates as a feed spool. In this embodiment, first spool 712 and second spool 714 are both driven together at the same rate and in the same direction, such as by an electric motor and a common chain, timing belt, or gear drive (e.g. with an intermediate gear between the gears for first spool 712 and second spool 714). Because the effective radii of first spool 712 and second spool 714 are roughly the same at the beginning of the stroke, the same amount of belt 716 is fed from second spool 714 as is taken up by first spool 712, and therefore pulley 718 rotates, but does not does not move laterally. As more belt 716 accumulates on first spool 712, its effective radius gets larger. Similarly, as more belt 716 is released from second spool 714, its effective radius gets smaller. With the effective radius of first spool 712 getting larger than that of second spool 714, more belt 712 is wound around first spool 712 than is released from second spool 714 with each turn of the two spools 712, 714. This action shortens the loop of belt 716 that extends around pulley 718, and therefore pulley 718 and second housing 722 are pulled (such as laterally pulled or rotationally pulled) towards spools 712 and 714 and first housing 720.

At the beginning of a stroke, winch actuator 710 is in a high torque, low speed mode. As winch actuator 710 progresses from a beginning of stroke configuration as shown in FIG. 6A towards an end of stroke configuration as shown in FIG. 6B, winch actuator 710 transitions from a high force, low speed configuration to a low torque, high speed configuration, pulling pulley 718 and second housing 722 faster towards first housing 720. In other words, the mechanical advantage of winch actuator 710 changes from the beginning of the stroke to the end of the stroke. In embodiments where linear movement is achieved by the actuator 710 (as shown in FIGS. 6A-6D), the mechanical advantage can be determined by the number of rotations of the first spool 712 required to provide a unit of linear movement. In embodiments where rotary movement of a joint is achieved by a harmonic actuator (such as described, for example, below with respects to FIGS. 8A-8C), the mechanical advantage can be determined by the winch ratio, which is equivalent to the speed of rotation of the first spool 712 to the speed of rotation of the joint.

Figure 6C:
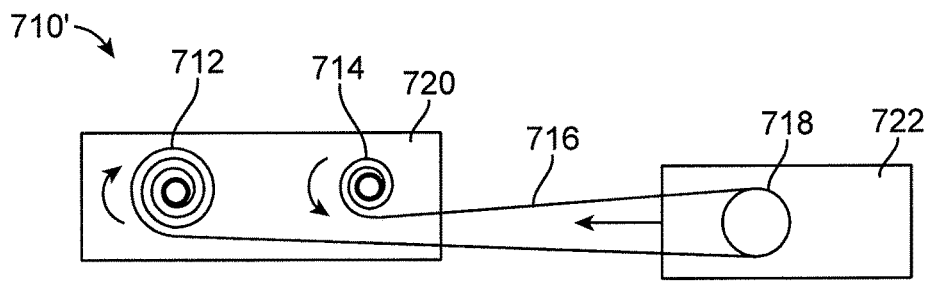
FIG. 6C is a side view of a variation of the actuator of FIGS. 6A and 6B wherein the first and second spools are gear coupled to rotate in opposite directions.
Figure 6D:
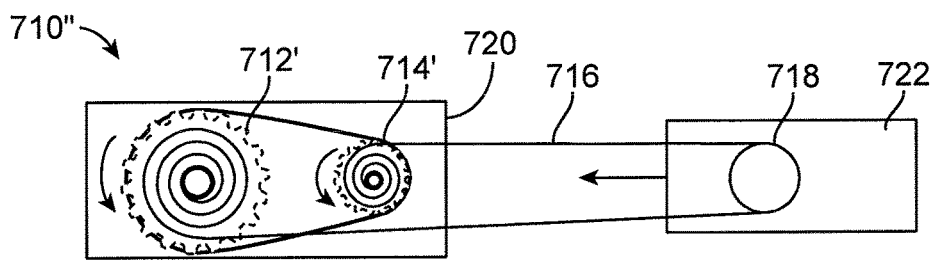
FIG. 6D is a side view of another variation of the actuator of FIGS. 6A and 6B wherein the first and second spools have different diameters and turn at different speeds.

Referring now to FIG. 6C, a variation of the harmonic winch of FIGS. 6A and 6B will be described. In this embodiment, first spool 712 and second spool 714 are configured to rotate in opposite directions. This can be accomplished, for example, by driving the two spools with gears directly coupled together. The harmonic winch actuator 710' in this embodiment operates in the same manner as actuator 710 of FIGS. 6A and 6B except that belt 716 is paid out from the bottom of second spool 714 instead of the top, such that a second spool 714 rotates in a counterclockwise direction to pay out belt 716, rather than in a clockwise direction as in FIGS. 6A and 6B.

Referring to FIG. 6 D, another variation 710" of the harmonic winch actuator of FIGS. 6A and 6B is shown. In this embodiment, first spool 712' and a second spool 714' have different diameters. For example, first spool 712' may have a diameter that is twice the diameter of second spool 714'. Additionally, the two spools 712', 714' are coupled to each other via gears or pulleys with the same diameter ratio as the diameter ratio of first spool 712' and second spool 714' in order to drive the spools in the same direction but at different rates. In this example, first spool 712' is driven at a rate that is half the rate of second spool 714'. With this arrangement, the second spool 714' pulls in belt 716 at a rate roughly the same as the rate that first spool 712' pays out belt 716 at the beginning of the stroke when both spools have roughly the same amount of belt 716 on them. As in other embodiments, the winch ratio increases as the amount of belt 716 on the pull spool 714' increases, and the amount of belt 716 on the feed spool 712' decreases. An advantage of this configuration is that the rate of winch ratio change is more gradual than when the spools are of the same diameter and driven at the same speed. This is because the diameter of feed spool 712' changes more slowly in this embodiment. As such, there is less variation in the winch ratio from the beginning of the stroke to the end of the stroke in this embodiment as compared with the previous embodiments.

In some embodiments, such as those shown depicted in FIGS. 6A-6D, a separate belt tensioner need not be provided. In these embodiments, first and second spools 712 and 714 may act as belt tensioners by pulling slack out of belt 716 when output pulley 718 is located in a position where no force is being put on belt 716. In other embodiments, no tensioner is necessary because tension is provided by an external tensioner or because there is always a force (such as gravity) pulling second housing 722 away from first housing 720. It is to be understood that the embodiments shown in FIGS. 6A-6D are simplified schematics and that any of the details described elsewhere in this disclosure can apply to the embodiments described with respect to FIGS. 6A-6D.

Referring now to FIGS. 7A and 7B, a side elevation view and a top plan view, respectively, of a more detailed embodiment of a harmonic winch actuator 710 are shown. Harmonic winch actuator 710 includes an electric motor 724 with a gear head 726 coupled to its output. Gear head 726 is provided with a motor drive sprocket 728 on its output. Drive sprocket 728 is coupled to a driven sprocket 730 with a motor drive chain 732. Driven sprocket 730 is twice the diameter of drive sprocket 728 in this embodiment to further reduce the rotational speed output by motor 724. This arrangement allows motor 724 to drive first spool 712. Further, first spool 712 and second spool 714 are each provided with a spool sprocket 734 of the same diameter and interconnected with inter-spool chain 736 such that they are both driven in the same direction and at the same speed of rotation by the motor 724. In the embodiment of FIGS. 7A and 7B, as was described in reference to FIGS. 6A and 6B, first spool 712 is shown on the left and serves as a pull spool while second spool 714 is shown on the right and serves as a feed spool. As before, pull spool 712 takes in belt 716 from the bottom while feed spool 714 pays out belt 716 from the top, and both spools 712, 714 turn clockwise to pull housing 722 towards housing 720. In contrast, when the spools 712, 714 are turned counter-clockwise, belt 716 is released more quickly by the first spool 712 than belt 716 is pulled in by the second spool 714. As a result, the length of the belt 716 between housing 722 and housing 720 is increased, and housing 722 is allowed to move away from housing 712.

Harmonic winch actuator 710 may also be provided with a belt tensioner 738 as shown to pull slack out of belt 716 during operation of winch actuator 710. In this embodiment, belt tensioner 738 is mounted between first spool 712 and second spool 714 and is configured to rotate up to about 180 degrees about an axis that is parallel to the axes of rotation of spools 712 and 714. Belt tensioner 738 may include a spiral torsion spring 740 located at one end as shown. Torsion spring 740 causes tensioner 738 to rotate and apply just enough force to belt 716 to remove the slack from the belt 716 without impeding the motion of the output pulley 718 and second housing 722 when no force is being applied by actuator 710. Belt tensioner 738 will subsequently be described in more detail with reference to FIGS. 9A-9C.

Rotational position sensors, such as encoders 742, may also be provided on belt tensioner 738 and motor 724 as shown. Encoder 742 may be used for position feedback to the electronics in order to control the sequencing of motor drive phases to motor 724 when it is a brushless 3-phase DC motor. The electronics may also use position information obtained from encoder 742, along with knowledge of the drive ratio from motor 724 to pull spool 712, to count rotations of the spools 712, 714. By doing so, the total length of the belt 716 between the spools 712, 714 can be determined. This information in turn can determine the maximum extended position of housing 722, which can be used to determine the maximum amount of flexion of an orthotic brace using the winch actuator 710 (such as orthotic brace 10, 300, 300', or 810 described herein). Moreover, belt tensioner 738 may be used in conjunction with encoders 742 to indicate to the controlling electronics and/or software the amount of slack in belt 716 at any given time during operation. When belt 716 is being pulled tightly, small variations in the position of the tensioner can be used to detect the force that is being applied by actuator 710.

In this exemplary embodiment, belt 716 can be 0.005 inches thick, 1 inch wide, and about 5 feet long. Belt 716 may be made out of a UHMWPE (ultra-high molecular weight polyethylene) such as Dyneema® or Spectra. Other suitable materials include PBO (poly(p-phenylene-2,6-benzobisoxazole)) such as Zylon, liquid crystal polymer such as Vectran, and para-aramids such as Kevlar®. Belt 716 may be made of a single, homogeneous material. Alternatively, belt 716 may be formed from laminated layers, coatings and/or woven or reinforcing fibers of the same or of different materials. It is beneficial to use a high-strength material and/or construct that can provide a sufficient tensile force without stretching, even with a small belt thickness. The thinner the belt 716 is, the smaller the effective radius change is as belt 716 moves from feed spool 714 to pull spool 712 of winch actuator 710. This means that more rotations of spools 712 and 714 are required to move pulley 718 and second housing 722 towards first housing 720 from the beginning of the stroke to the end of the stroke. In other words, a higher mechanical advantage and ratio are provided by using a thinner belt 716 in actuator 710.

Figure 8A:
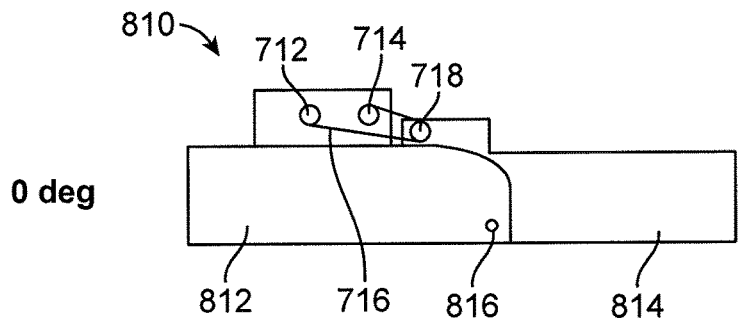
FIGS. 8A-8C are a sequence of side views showing the use of a harmonic winch on an orthosis having a single pivot point.
Figure 8B:
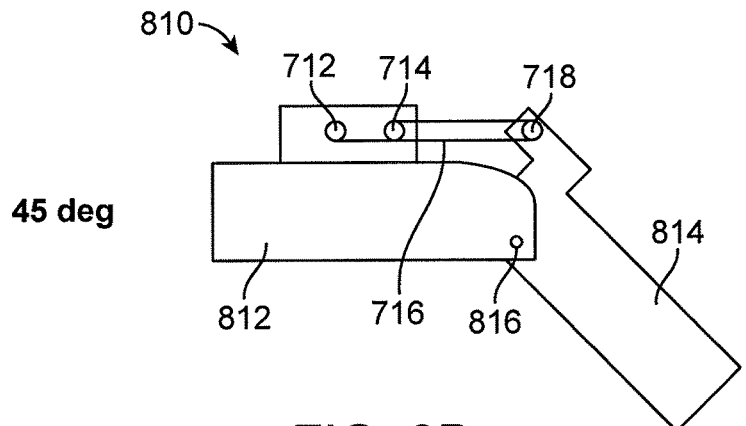
Figure 8C:
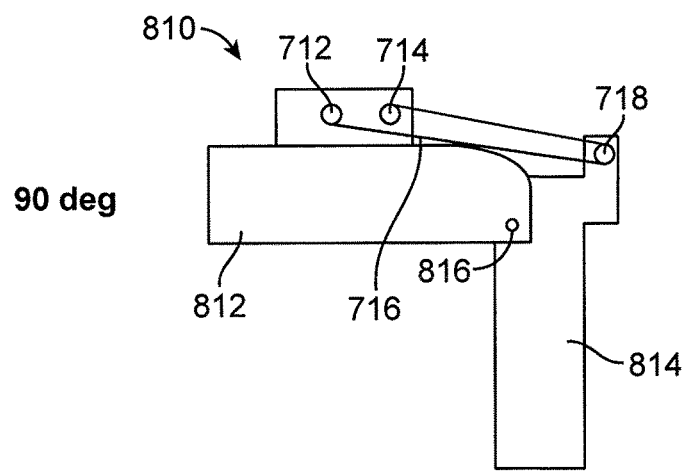

Referring to FIGS. 8A-8C, harmonic winch actuator 710 is shown coupled to an exemplary joint assistance device 810. Device 810 may be an orthosis configured to attach adjacent to a patient's knee and actively assist the patient with walking and/or other leg movements, as described above with respect to FIGS. 1 and 2. A first portion 812 of device 810 is configured to attach to the patient on one side of the joint, such as above the knee on the thigh, as previously described. A second portion 814 is configured to attach to the patient on an opposite side of the joint, such as below the knee on the calf. In this embodiment, the first portion 812 and the second portion 814 of device 810 are rotatably coupled together by a single pivot point 816. However, the first and second portions 812 and 814 need not be connected by a single pivot point, as will be subsequently described with reference to other embodiments. As shown in FIG. 8A-8C, first and second spools 712 and 714 may be located on the first portion 812 of device 810. Output pulley 718 may be located on the second portion 814 of device 810 as shown. In other embodiments, the locations of these components may be reversed. In operation, pivot point 816 can be located adjacent to the knee or other joint. Belt 716 loops around second spool 714 and spans between first portion 812 and second portion 814 of device 810.

The harmonic winch actuator 710 can be used to rotate the second portion 814 of the device 810 relative to the first portion 812. For example, the winch actuator 710 can be used to provide assistance during extension of the patient's leg (and thus decreasing the angle formed by the device 810). FIG. 8C shows device 810 in a bent configuration where the first portion 812 forms an angle of 90° with second portion 814, such as when the patient is sitting. In this position, the belt 716 is relatively long between the first portion 812 and the second portion 814. As the actuator rotates the spools 712, 714, the diameter of the spool 712 can increase while the diameter of the spool 714 decreases, thereby causing the length of the belt 716 to decrease between the first portion 812 and the second portion 814. This shortening of the belt 716 causes the upper sections of the first and second portions 812, 814 to move closer together by pivoting around the pivot point 816. FIG. 8A shows device 810 move into a straight configuration wherein the first portion 812 forms an angle of 0° with second portion 814. The winch actuator 710 can thus be used to assist the patient in extending a leg from sitting (approximately 90° to approximately 0°). Likewise, the harmonic winch actuator 710 can be used to extend the leg during walking. For example, FIG. 8B shows device 810 in a partially bent configuration wherein the first portion 812 forms an angle of 45° with second portion 814. This orientation may occur during the patient's stride when walking. Similar to as described with respect to FIG. 8C, the actuator can be used to shorten the length of the belt 716, thereby pulling the upper sections of the first and second portions 712, 714 together about the pivot point 816, thereby assisting in extending the leg to 0° as shown in FIG. 8A.

In some embodiments, to flex the leg when wearing the device 810, the belt 716 can be loosened by rotating the rollers 712, 714 in the opposite direction. Loosening the belt 716 (or creating slack in the belt 716) in turn allows the upper sections of the first and second portions 812, 814 to move apart from one another about the pivot point 816, thereby allowing the leg to flex. The winch actuator 710 can therefore advantageously provide assisted extension of the device 810 while allowing free flexion of the device. Moreover, the device 810 can be set to provide both free (unassisted) extension and flexion by simply extending the belt 716 fully for both extension and flexion.

In the exemplary embodiment of FIGS. 8A-8C, device 810 as a range of motion of about 90°. In other embodiments, the range of motion may be more or less than 90°.

Figure 8D:
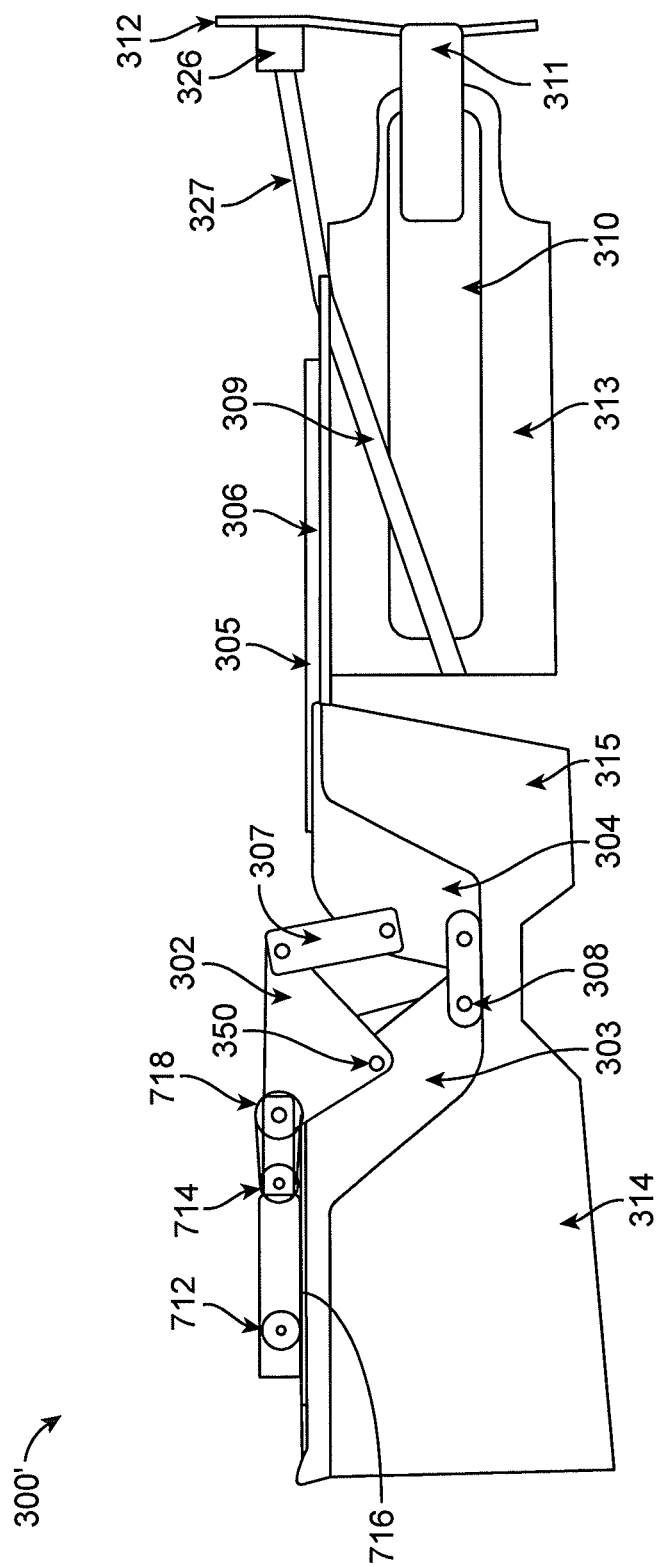
FIG. 8D is a side view showing the use of a harmonic winch on an orthosis having a polycentric hinge.

Referring to FIG. 8D, a harmonic winch actuator 710 is shown mounted to a multi-fit orthotic system 300' similar to system 300 originally shown in FIG. 2. As shown, first spool 712 and second spool 714 of actuator 710 are located on thigh portion 303 of orthosis 300'. Output pulley 718 is coupled to bell crank 302 such that when belt 716 pulls output pulley 718 towards the spools 712, 714, bell crank 302 is rotated counter-clockwise around pivot point 350. Bell crank 302 in turn pulls linkage 307, which rotates calf portion 304 about dual pivot coupling 308 to the straight or 0° position shown. Dual pivot coupling 308 forms a polycentric hinge which allows calf portion 304 to pivot about two axes with respect to thigh portion 303 of orthosis 300'. This method of orthosis 300' articulation with the polycentric hinge more closely mimics the articulation that naturally occurs in the adjacent knee of the patient.

Figure 9A:
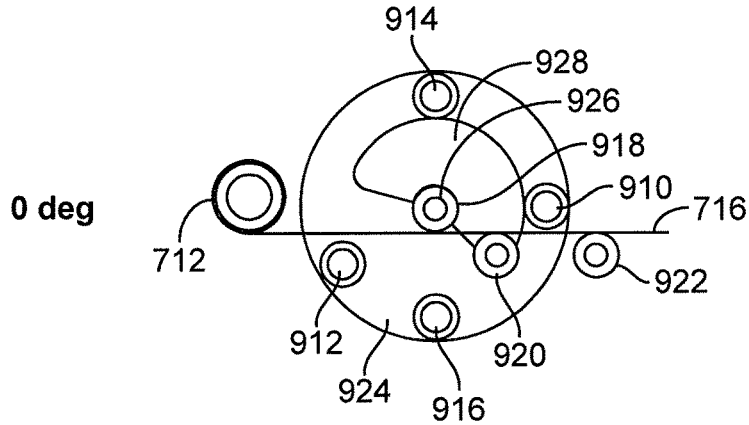
FIGS. 9A-9C are a sequence of side views showing details of a belt tensioner of the actuator shown in FIGS. 7A-7B.
Figure 9B:
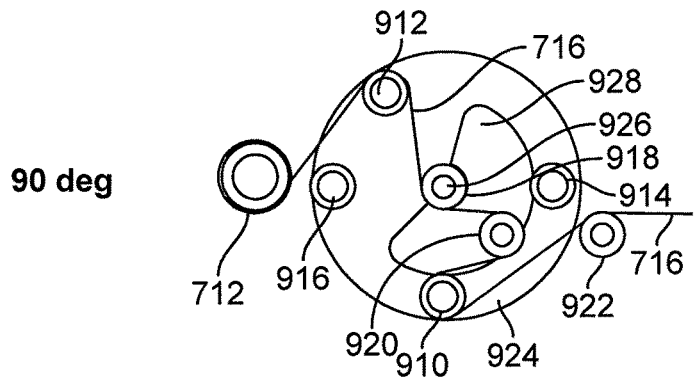
Figure 9C:
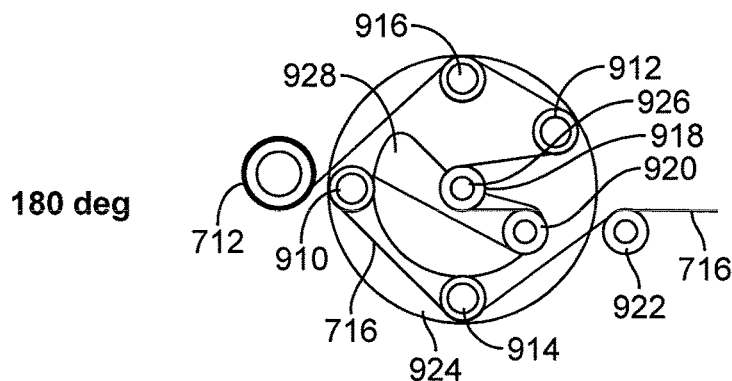

Referring to FIGS. 9A-9C, detailed construction and operation of the exemplary belt tensioner 738 first introduced with reference to FIGS. 7A and 7B will now be described. In this embodiment, tensioner 738 includes four moving rollers 910, 912, 914 and 916 and three fixed rollers 918, 920 and 922. Each of the moving rollers 910, 912, 914, 916 and the fixed rollers 918, 920, 922 may be configured to rotate about its own axis, such as on bearings, to reduce friction as belt 716 moves with respect to the respective roller. Additionally, the moving rollers 910, 912, 914 and 916 are mounted on a drum 924 or disk such that they rotate with drum 924 about its central axis 926. In this embodiment, drum 924 may rotate through a range of about 180°. Slot 928 is provided through drum 924 to allow fixed roller 920 to protrude through drum 924 without impeding its range of rotation. FIG. 9A shows tensioner 738 in a 0° position with belt 716 passing through tensioner 738 in a straight or nearly straight path. FIG. 9B shows tensioner 738 in a 90° position with belt 916 being drawn around fixed rollers 918, 920 and 922 by moving rollers 910 and 912. FIG. 9C shows tensioner 738 in a 180° position with belt 916 being drawn further around fixed rollers 918, 920 and 922 by moving rollers 910, 912, 914 and 916. With this arrangement of rollers, the belt 716 at no point touches another portion of the belt 716 and rests only on rolling supports, thus avoiding friction and wear of the belt 716. It can be appreciated that the serpentine belt path shown in FIG. 9C is considerably longer than the straight belt path shown in FIG. 9A. As such, tensioner 738 is able to take up a large amount of slack in belt 916 without rotating very far.

During operation of the harmonic winch actuator 710 when belt 716 is applying a load to the output pulley 728, belt tensioner 738 is typically in an orientation close to the 0° state shown in FIG. 9A. In this state, moving rollers 910 and 912 contact belt 716 and deflect it by a small amount, even when high force is being exerted by the winch actuator 710. By measuring the small amount of belt deflection with the previously mentioned encoder, the system controller can determine the amount of force being exerted by belt 716 on the output pulley. As tension in belt 716 drops off, such as when a patient moves his leg ahead of the position being driven by the harmonic winch actuator, belt tensioner 738 rotates up to 180° to take up the belt slack. The tensioner rotation is provided automatically by spiral torsion spring 740, shown in FIGS. 7A and 7B.

Figure 10A:
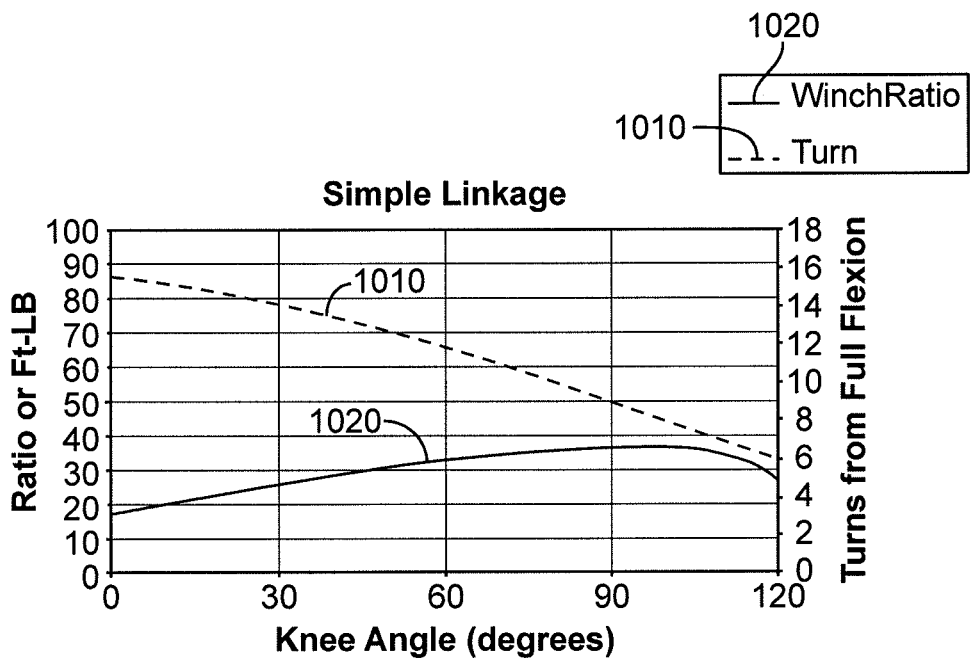
FIG. 10A is a graph showing the relationship of various parameters to the joint angle for a simple linkage orthosis.

FIG. 10A is a graph showing the relationship of torque, effective ratio and number of spool turns from full joint flexion in the exemplary harmonic winch actuator 710 as a function of knee angle for an orthosis having a fixed radius joint linkage (in other words, a joint linkage such as shown in FIGS. 8A-8C). In this graph, it is assumed that the linear motion of actuator 710 is converted directly to rotary motion of the output joint at a radius of 1.3 inches from the single rotation axis of the joint. The graph line 1010 showing the number of spool turns shows the number of turns starting at 6 and increasing to about 16 turns. The first through fifth spool turns are not shown on the graph, since at this point the effective diameters of the spools are nearly equal, creating an effective winch ratio near infinity. In other words, when the spools are exactly the same diameter, the amount of belt paid out and pulled in is the same and the same-diameter spools could be rotated an infinite number of times without changing the belt path length. Dividing the pull spool speed by the zero speed of the joint gives an infinite ratio that produces almost no output movement.

The graph line 1020 shows the effective winch ratio going from about 18, increasing to about 37 and dropping back down to about 28 over the course of the winch stroke. This shows that there is a mechanical advantage wherein the rotation of the spools is at least 18 times faster than the rotation of the orthosis joint. In some embodiments, a gear head 726 may be used that, when coupled with drive sprocket 728 and driven sprocket 730 as shown in FIGS. 7A-7B, produces a gear ratio of 12.9 to 1. When this front end gear ratio of 12.9 is multiplied by the winch ratios shown in FIG. 10A, total reduction ratios ranging from about 232 to about 477 are achieved in this exemplary embodiment. These high ratios are used to go from the rotation of the high-speed motor to the slow but high torque rotation needed to move a person's leg. Graph line 1020 of FIG. 10A also shows that when a patient's leg is bent between 60° and 120°, and more particularly when it is bent at about 90°, the exemplary harmonic winch actuator is configured with a high winch ratio to provide higher torque at lower speeds, such as when a patient is moving from a sit to a standard position or is climbing stairs. Conversely, when a patient's leg is bent less than 30°, the actuator provides a lower winch ratio with less torque and more speed, such as when a patient is walking fast.

Figure 10B:
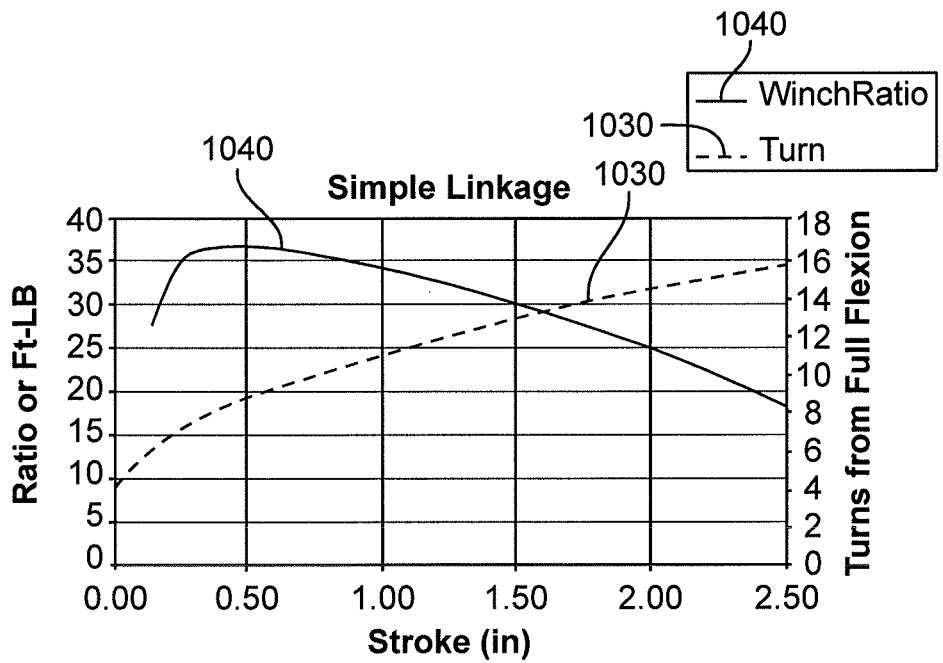
FIG. 10B is a graph showing the relationship of various parameters to the actuator stroke for a simple linkage orthosis.

FIG. 10B is a graph similar to that of FIG. 10A, but the relationship of torque, effective ratio and number of spool turns is shown as a function of actuator stroke rather than knee or joint angle. Graph line 1030 shows the number of spool turns made from the beginning of the stroke. Graph line 1040 shows the effective winch ratio over the course of the actuator stroke. Graph line 1040 shows that near the beginning of the actuator stroke (which corresponds to a high joint angle in FIG. 10 A), the exemplary actuator provides a high reduction ratio and high torque. Conversely, near the end of the stroke (which corresponds to a low joint angle in FIG. 10 A), the actuator provides a low reduction ratio and low torque, which allows for higher speed.

Figure 11A:
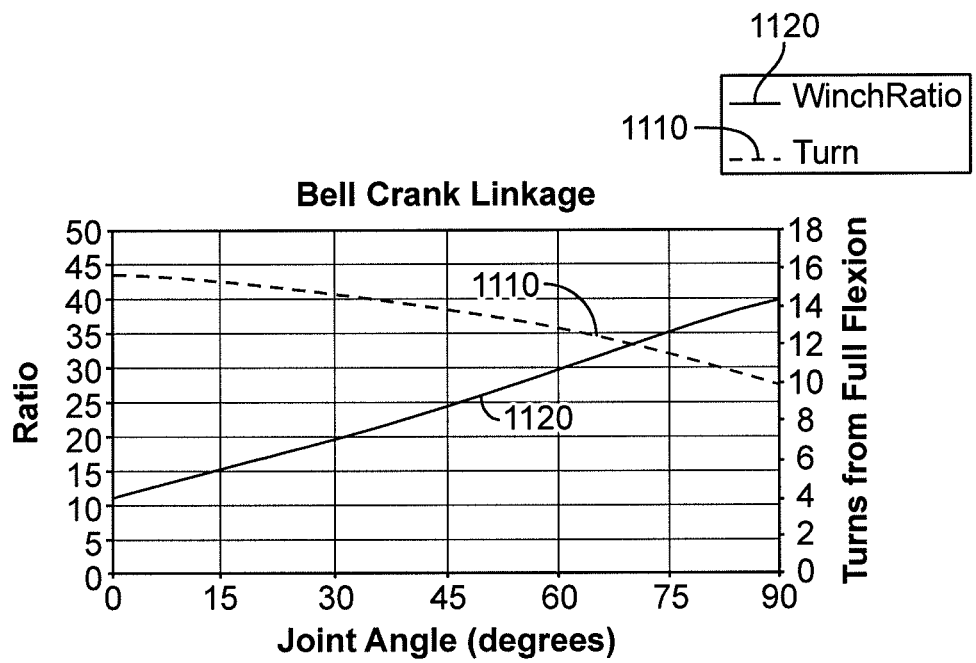
FIG. 11A is a graph showing the relationship of various parameters to the joint angle for an orthosis having a bell crank linkage.

FIG. 11A is a graph similar to that shown in FIG. 10A, but for an orthosis having a bell crank type linkage (such as shown in FIG. 8D) instead of a fixed radius linkage. Graph line 1110 shows the relationship between the number of spool turns as a function of joint angle. Graph line 1120 shows the relationship between the winch ratio as a function of joint angle. Both graph lines show the interaction between the linkage and the harmonic winch actuator. As before, this graph shows that the actuator provides a high reduction ratio with high torque when the patient's leg is bent at a high angle such as 90°, and a much lower reduction ratio with lower torque and therefore higher speed when the patient's leg is straight or close to being straight (i.e. at 30° or less), such as during the swing phase of a walking gait.

Figure 11B:
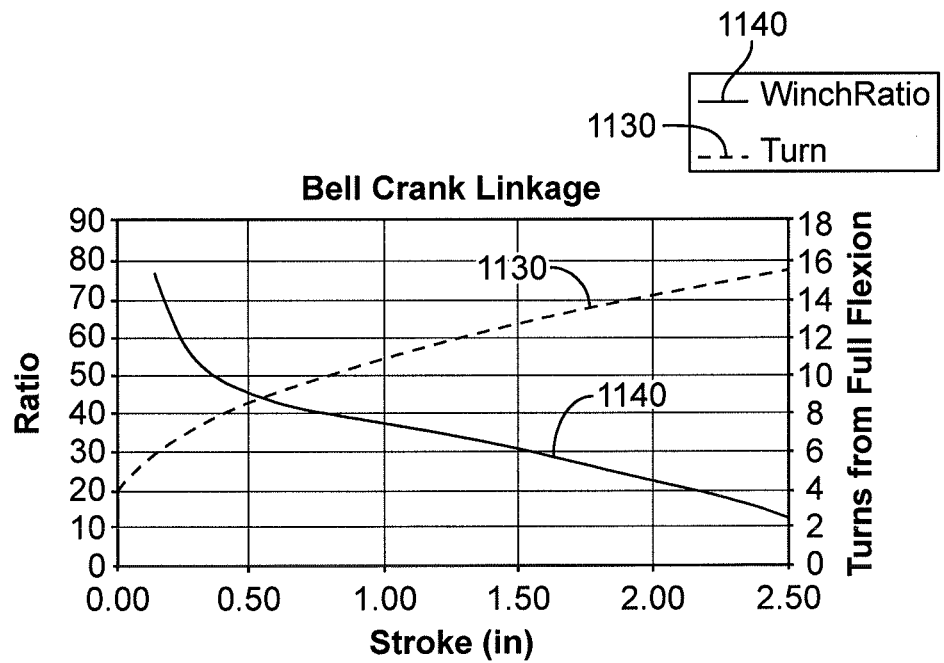
FIG. 11B is a graph showing the relationship of various parameters to the actuator stroke for an orthosis having a bell crank linkage.

FIG. 11B is a graph similar to that shown in FIG. 11A, but the relationship of torque, effective ratio and number of spool turns is shown as a function of actuator stroke rather than knee or joint angle. Graph line 1130 shows the number of spool turns from the beginning of the stroke. Graph line 1140 shows the effective winch ratio over the course the actuator stroke.

Figure 12A:
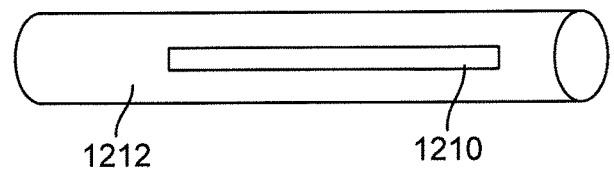
FIGS. 12A-12C are various views showing details of an embodiment for attaching the ends of a belt of a harmonic winch to the spools.
Figure 12B:
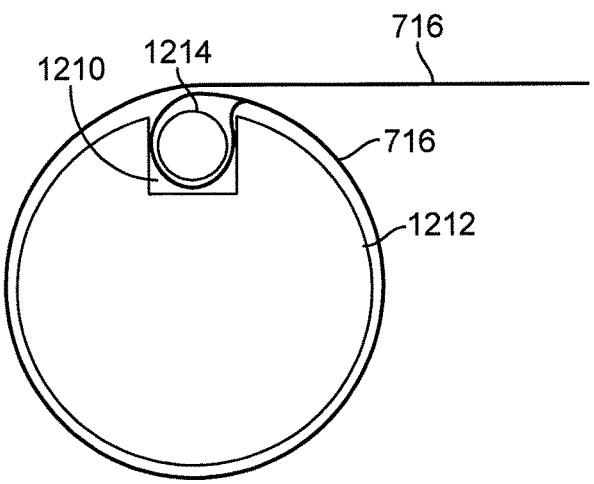
Figure 12C:
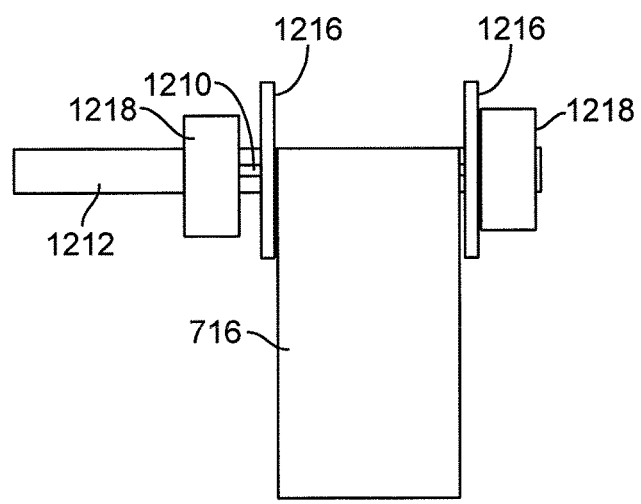
Figure 14:
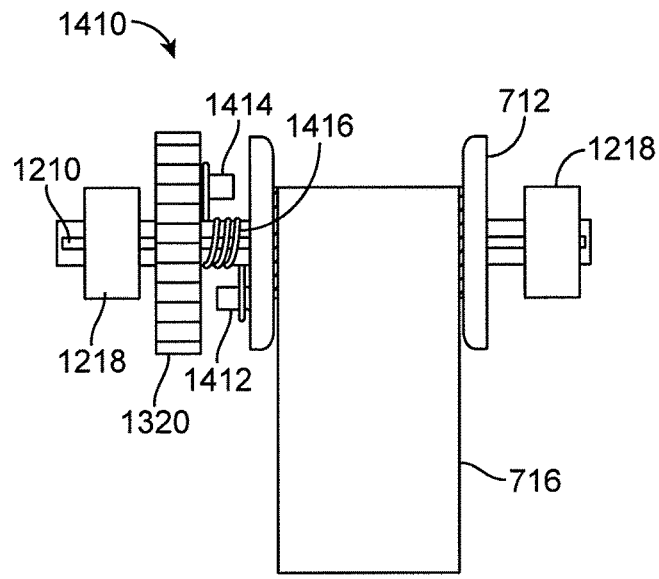
FIG. 14 shows various details of an alternative spool-mounted belt tensioner.
Figure 14A:
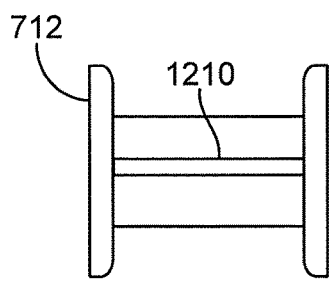
FIG. 14A shows a close-up of the front of the spool with a belt keyway of FIG. 14.
Figure 14B:
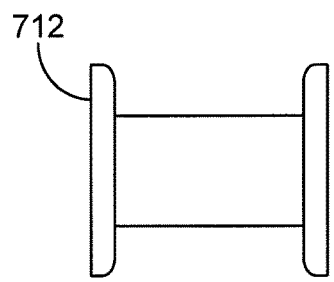
FIG. 14B shows the back of the spool of FIG. 14A.
Figures 14C, 14D, 14E:
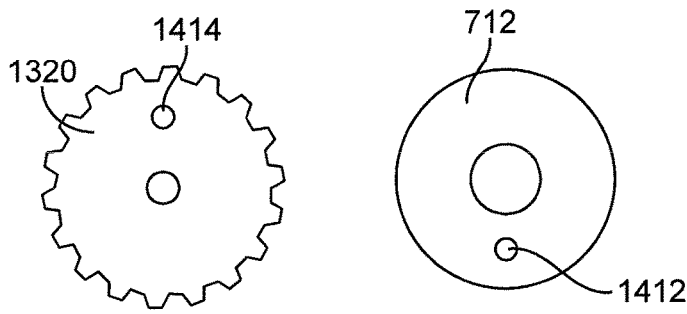
FIG. 14C shows the gear with stop of FIG. 14.
FIG. 14D shows the spool with stop of FIG. 14.
FIG. 14E shows the belt with end loop of FIG. 14.

Referring to FIGS. 12A-12C, details of one option of attaching belt 716 to the spools of the exemplary harmonic winch actuator are shown. As best seen in FIG. 12A, a longitudinally oriented keyway 1210 may be provided along all or a portion of the length of central shaft 1212 that forms the center of previously described first spool 712 and second spool 714. Keyway 1210 is sized to receive a key 1214 along with an end portion of belt 716. In some embodiments, a permanent loop may be constructed at the end of belt 716, as shown in FIG. 12B. To attach the end of belt 716 to shaft 1212, key 1214 is slid into the loop and placed into keyway 1210. In other embodiments, the end of the belt 716 may not include a loop but is wrapped at least 180° around key 1214. After key 1214 is placed into keyway 1210, several wraps of belt 716 are then turned around shaft 1212 to help hold key 1214 in place in keyway 1210. As shown in FIG. 12C, two washers 1216 and or two bearings 1218 may be slid along shaft 1212 to cover each end of key 1214 to further lock the key in place. In other embodiments (not shown), the cross-section of the shaft keyway 1210 may be narrower at its outer opening so that it is wide enough only for belt 716 to pass therethrough, but not wide enough to allow key 1214 to exit outwardly from the keyway. In these embodiments, key 1214 and the end portion of belt 716 are slid longitudinally into the keyway during assembly. In each of the above-described embodiments, the ends of belt 716 are securely fastened to the central shaft 1212 of each of the spools so that they do not slip even when high loads are applied to the belt.

Referring to FIGS. 13A and 13B, another embodiment of harmonic winch actuator is shown. In this embodiment, actuator 1310 includes a motor 724 that drives a pinion gear 1312. Pinion gear 1312 drives a larger gear 1314 attached to one end of an idler shaft 1316. At the other end of idler shaft 1316, another pinion gear 1318 drives a spool gear 1320. Gears 1312, 1314, 1318 and 1320 are sized relative to one another to provide the desired amount of gear reduction between motor 724 and first spool 712. Second spool 714 is also provided with a spool gear 1320 that meshes with the spool gear 1320 of the first spool 712, such that first spool 712 drives second spool 714 at the same speed but in an opposite direction through the gears 1320. In this embodiment, belt 716 wraps around the bottom of first spool 712 and second spool 714 such that first spool 712 serves as a pull spool and second spool 714 serves as a feed spool. A guide roller 1322 may also be provided between second spool 714 and output pulley 718.

Referring to FIGS. 14A-E, details of a spool-mounted belt tensioner 1410 are shown. While only first spool 712 is shown, the construction and operation of second spool 714 is a mirror image of that of first spool 712. In this embodiment, one flange of spool 712 is provided with an outwardly protruding shaft stop 1412. Spool gear 1320 is similarly provided with an inwardly protruding spool stop 1414. A torsion spring 1416 may be provided between shaft stop 1412 and spool stop 1414. In operation, spool gear 1320 only drives spool 712 when spool stop 1414 rotationally engages with shaft stop 1412. When spool stop 1414 is not engaged with shaft stop 1412, torsion spring 1416 rotates spool 712 to pull slack out of belt 716. When force is being applied, belt torque is applied to shaft 1212 through keyway 1210 and key 1214. If the belt 716 is slack and an external force is applied at 722, spools 712 and 714 rotate in opposite directions until they encounter the spools stops. At that point, chain or belt 1512 is tight and prevents further movement of the output. Once the belt 716 is not slack, further movement of the output depends on rotation of the different diameters of the winds on the spools. In other words, spools 712 and 714 rotate in opposite directions while applying force, and in the same direction to pull out slack. In this embodiment, each spool-mounted tensioner 1410 is configured to pull in belt slack equivalent to one wrap of the belt 716 around the spool 712. This embodiment can advantageously have a smaller size due to the elimination of the separate tensioner.

Figure 15A:
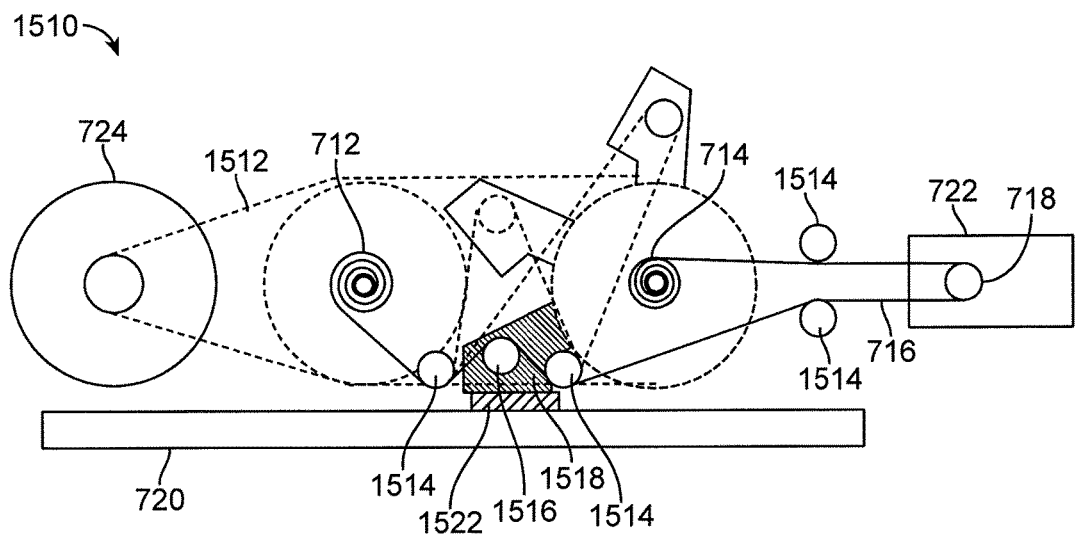
FIG. 15A is a side elevation view showing another exemplary embodiment of a harmonic winch actuator.
Figure 15B:
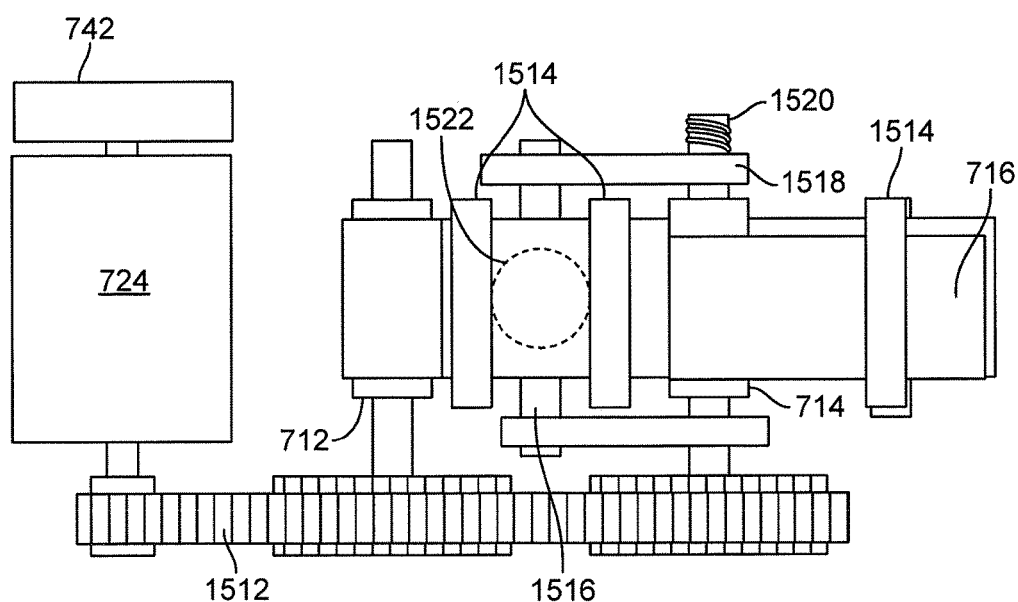
FIG. 15B is a top plan view showing the actuator of FIG. 15A.

Referring to FIGS. 15A and 15B, another embodiment of a harmonic winch actuator 1510 is shown. In this embodiment, actuator 1510 includes a timing belt 1512 to drive first spool 712 and second spool 714 at the same speed and in the same direction. First spool 712 serves as a pull spool while second spool 714 serves as a feed spool. Two fixed-position guide rollers 1514 may be provided between first spool 712 and second spool 714. A movable-position guide roller 1516 may be provided on a rotating arm 1518 which pivots about the same axis as the second spool 714. A torsion spring 1520 may be provided on rotating arm 1518 to bias it in a clockwise direction. Tension on belt 716 will bias rotating arm 1518 in a counterclockwise direction towards the position shown in FIG. 15A. When slack occurs in belt 716 during operation, rotating arm 1518 with movable roller 1516 will rotate clockwise to the various positions shown in phantom line in FIG. 15A to take up the slack in belt 716 by increasing the length of the belt path. A load cell 1522, or other force sensor such as a pressure sensitive resistor, may be provided beneath rotating arm 1518 to measure the tension in belt 716 when there is no slack in the belt.

Figure 16A:
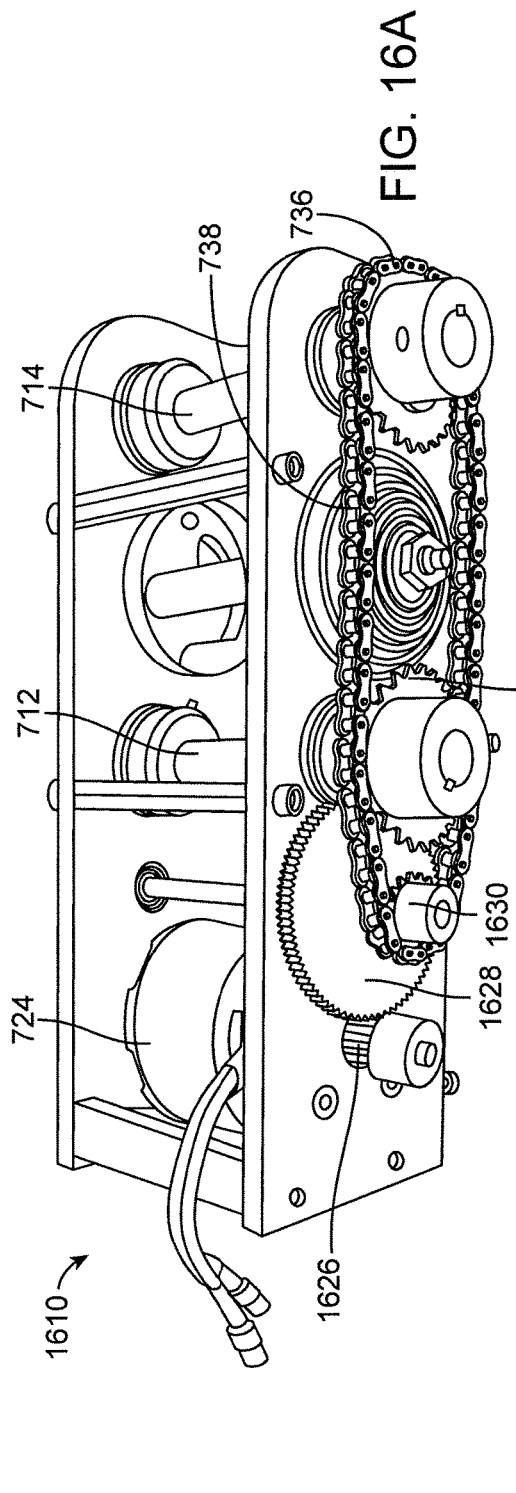
FIGS. 16A-16B show another exemplary harmonic winch actuator.
Figure 16B:
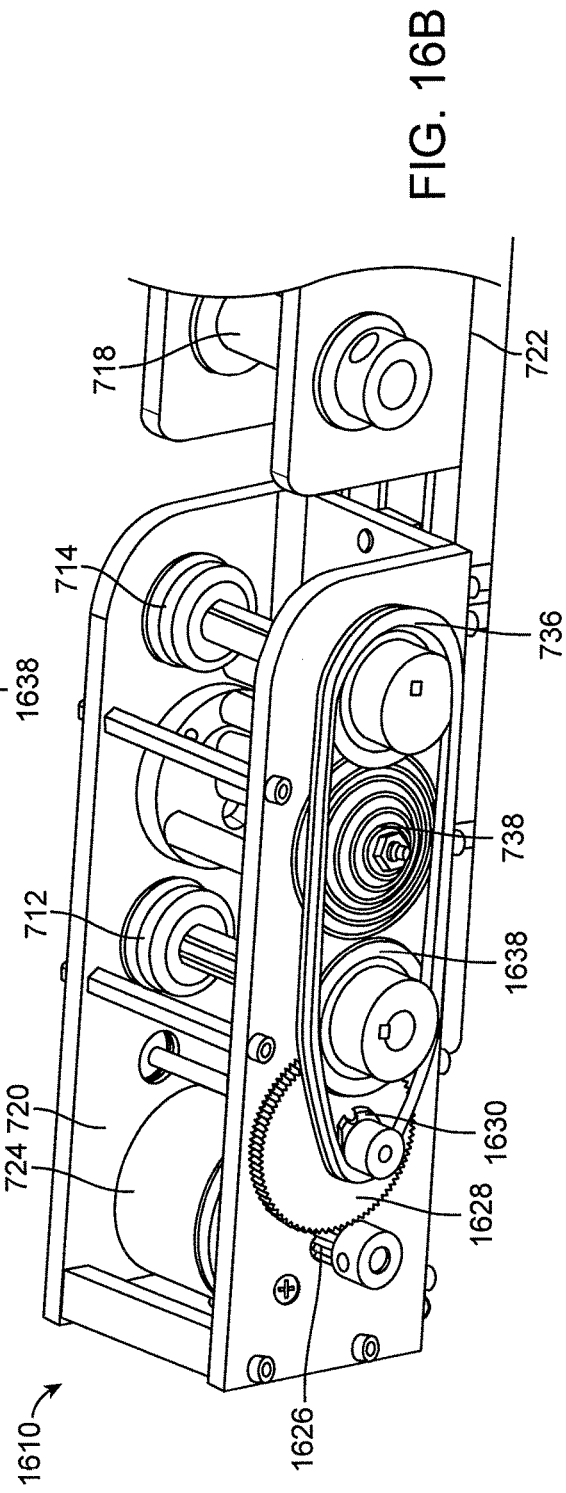

Referring to FIGS. 16A and 16B, another embodiment of a harmonic winch actuator 1610 is shown. The harmonic winch actuator 1610 is similar to the winch actuator 710 of FIGS. 7A-7B with a few differences. In this embodiment, the motor 724 drives a pinion gear 1626, which in turn drives an intermediate gear 1628. The intermediate gear is coupled to a sprocket 1630, which in turn drives a belt or chain 736 (shown as a chain in FIG. 16A and a belt in FIG. 16B). Rotation of the belt or chain 736 then causes the pull spool 712 to rotate through a sprocket 1638. The winch actuator 1610 thus eliminates the gearhead of FIG. 7A, which can provide a wider range of gear ratios, but can also be more expensive than the coupling gears of system 1610.

Figure 17A:
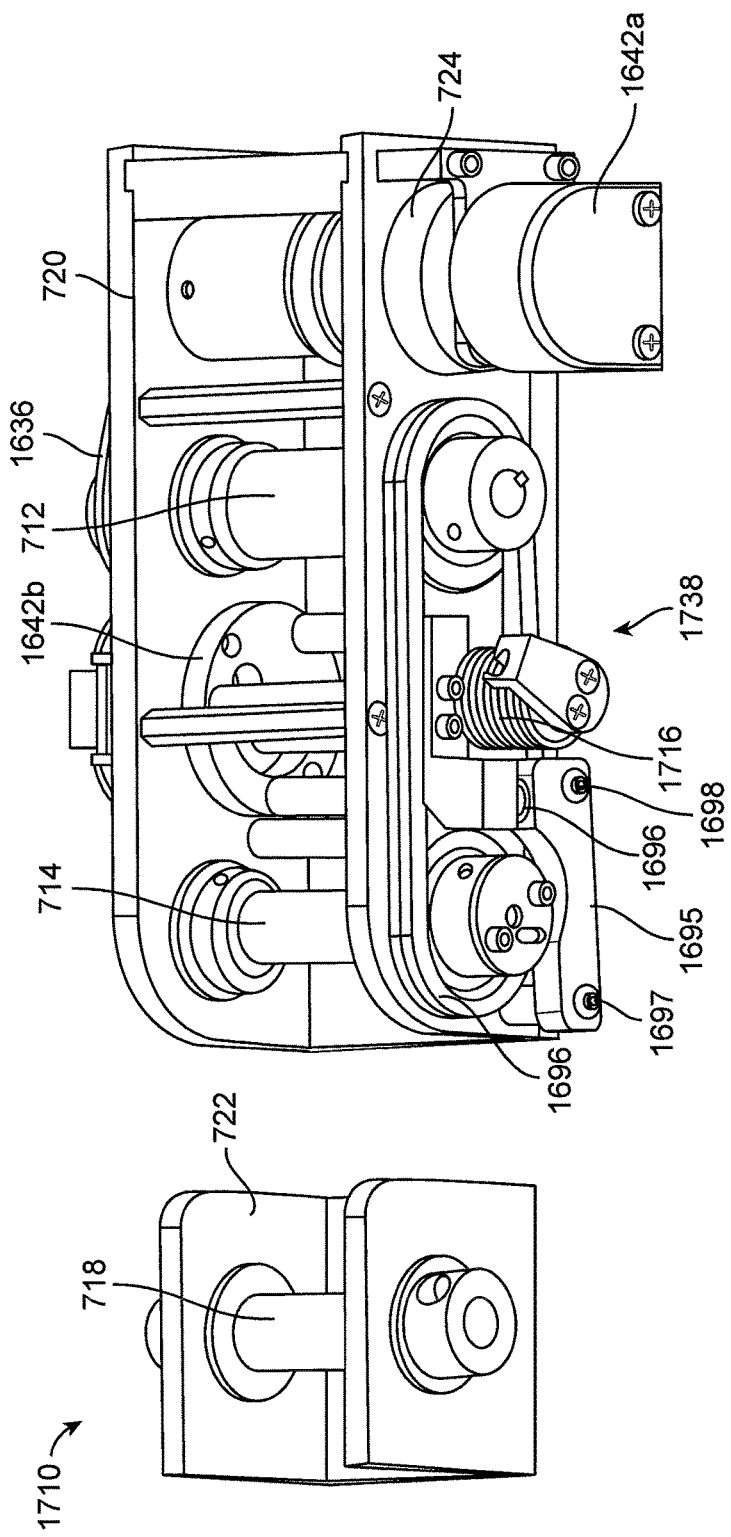
FIGS. 17A-17B show two different views of another exemplary harmonic winch actuator.
Figure 17B:
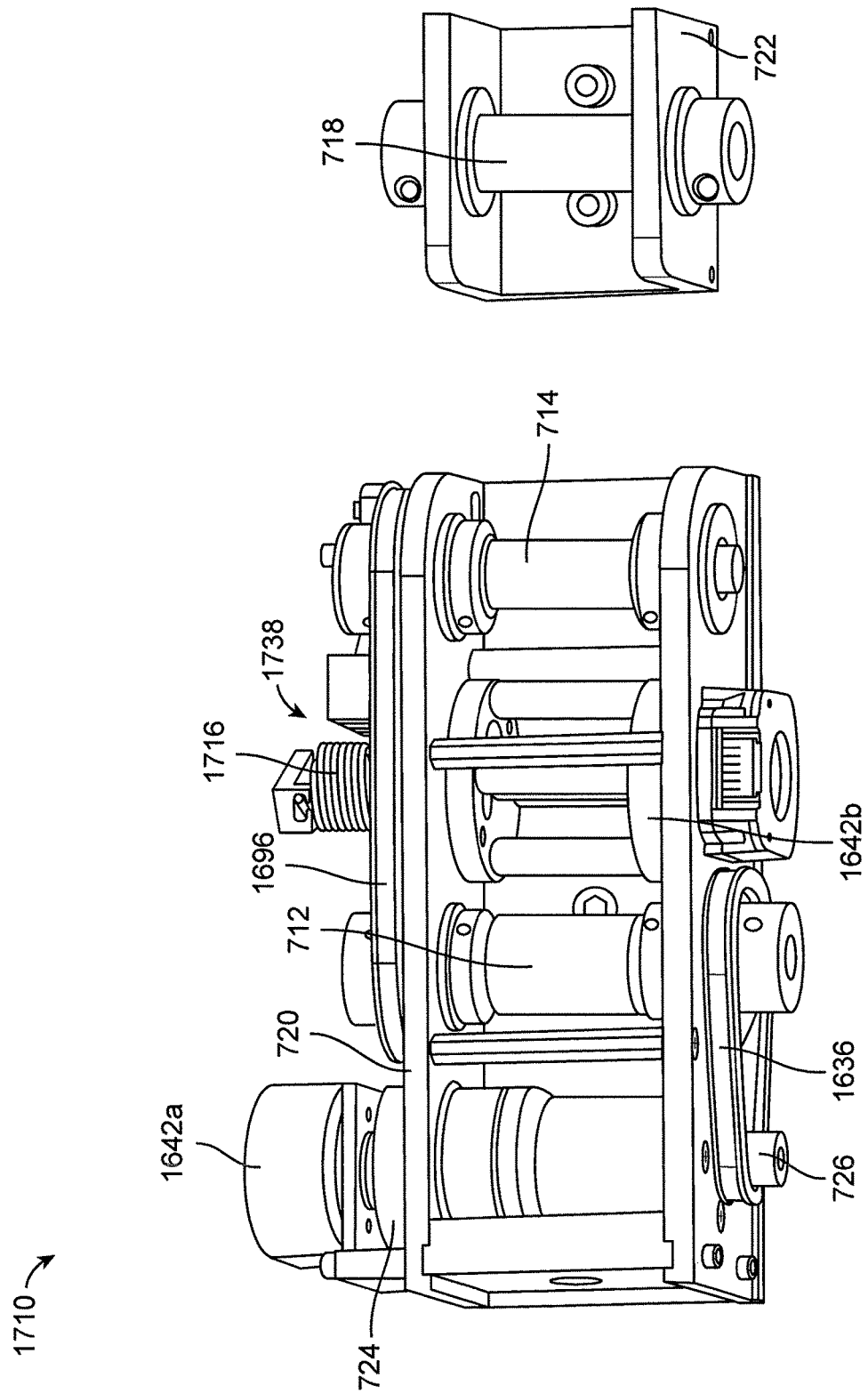

Another embodiment of a harmonic winch actuator is shown in FIGS. 17A and 17B. This embodiment is similar to the winch actuator 710 of FIGS. 7A and 7B, but the belt tensioner 1738 includes a standard torsion spring 1716 instead of a spiral torsion spring. Further, in contrast to winch actuator 710, in this embodiment, the spring 1738 is on the same side of the housing 720 as the motor encoder 1642a while the tensioner encoder 1642b is on the opposite side of the housing 720 as the spring 1716. Further, actuator 1710 includes a first chain 1636 (coupling the gearhead pinion 726 to the pull spool 712) and a second chain 1696 (coupling the pull spool 712 to the feed spool 714) on opposite sides of the housing 720. Finally, an additional tensioner 1695 is coupled with the chain 1696. Coupled with the tensioner 1695 are a chain tensioner spring 1696, a chain tensioner pivot shaft 1697, and a chain tensioner sprocket shaft 1698. The tensioner 1695 can advantageously allow for the relaxation of the required tolerances in placement of the sprockets and allows for stretching of the chain 1696 over time.

The actuator 12 (such as the winch actuator described herein) can be coupled to an orthosis to provide the force needed to assist or resist the leg muscle(s). Although it is intended to be relatively small in size, the actuator 12 may be located on the lateral side to avoid interference with the other leg. The actuator 12 may also be located on an anterior region to allow a single orthotic device to be used no either the right or left leg of a patient. The actuator 12 may be coupled to both the upper and lower portions 16, 14 of the structural frame to provide assistance and/or resistance with leg extension and/or flexion. If the center of rotation of the actuator is located a distance away from the joint, a variety of coupling mechanisms can be used to couple the actuator to a portion of the orthosis on the other side of the joint. The coupling mechanism can be constructed using belts, gears, chains or linkages as is known in the art. These couplings can optionally change the ratio of actuator rotation to joint rotation.

In the above-described embodiments, the exemplary harmonic winch actuators described are described as driving an orthosis in only one direction: extension of the joint. In other embodiments (not shown), the actuator may be configured to drive the joint in another direction, such as flexion of the joint by coupling between the inside parts of the hinge or by using pulleys to reverse the motion and push on a rigid linkage to force flexion. In some embodiments, more than one harmonic winch actuator may be provided on the orthosis for driving it in more than one direction, with one coupling the inside and another coupling the outside of the joint, or with one pushing and the other pulling on the linkage. In some embodiments, the orthosis may be driven in one direction by the harmonic winch actuator and driven in the opposite direction by the patient, gravity, a biasing spring, or some other form of actuator.

While the actuator and orthosis are described above as being used primarily with the knee, application to other joints is possible. For instance, a device to aid in wrist movement may have elastic bands coupling a small actuator to the hand and wrist. Joints with more than one degree of freedom may have a single device to assist/resist the primary movement direction, or may have multiple actuators for different degrees of freedom. Other potential candidates for assistance include the ankle, hip, elbow, shoulder and neck.

The above described orthosis, components and methods provide a light weight active muscle assistance system. Although the systems have been described in considerable detail with reference to certain embodiments thereof, other versions are possible. For example, any feature disclosed in connection with any particular embodiment can be combined with any other feature disclosed in any other embodiment. Therefore, the spirit and scope of the appended claims should not be limited to the description of the exemplary versions contained herein.

What is claimed is:

1. An active assistance orthosis comprising:
   a first portion configured to attach to a patient on one side of a joint;
   a second portion configured to attach to the patient on an opposite side of the joint; and
   an actuator configured to apply a force between the first and the second portions of the orthosis, the actuator comprising:
      a first spool rotatably mounted to the first portion;
      a second spool rotatably mounted to the first portion;
      an output pulley mounted to the second portion; and
      a belt having a first end wrapped around the first spool, a second end wrapped around the second spool, and a mid-portion wrapped around the output pulley,
      wherein the actuator is configured to rotate the first spool and the second spool, the rotation of the first spool pulling the belt a given length and the rotation of the second spool feeding the belt less than the given length so as to pull the output pulley towards the first portion, wherein pulling the output pulley towards the first portion pulls at least part of the second portion towards at least part of the first portion.

2. The orthosis of claim 1, wherein the actuator further comprises a belt tensioner configured to take up slack in the belt.

3. The orthosis of claim 2, wherein the belt tensioner comprises a rotatable disk separate from the first spool, the second spool and the output pulley.

4. The orthosis of claim 3, wherein the rotatable disk comprises at least one moving roller configured to interact with at least one fixed roller to increase a belt path length.

5. The orthosis of claim 3, wherein the belt tensioner comprises a rotational position sensor coupled to the rotatable disk, and wherein the sensor is configured to communicate with a controller to indicate a belt tension when there is no slack in the belt.

6. The orthosis of claim 1, further comprising a hinge coupling the first portion to the second portion, and wherein pulling at least part of the second portion towards at least part of the first portion comprises rotating the first portion relative to the second portion about the hinge.

7. The orthosis of claim 6, wherein the actuator is configured to provide a winch ratio between a rate of first spool rotation and a rate of orthosis hinge rotation, and wherein the winch ratio is higher when the orthosis is bent than when it is straight.

8. The orthosis of claim 6, wherein the actuator is configured to provide a first winch ratio when the orthosis is positioned at about a 90° angle and a second winch ratio when the orthosis is positioned at about a 0° angle, and wherein the first winch ratio is more than twice the second winch ratio.

9. The orthosis of claim 6, wherein the actuator is configured to apply a lower torque and higher speed as a hinge angle between the first portion and the second portion decreases.

10. The orthosis of claim 1, further comprising a polycentric hinge coupling the first portion to the second portion.

11. The orthosis of claim 10, further comprising a bell crank linkage coupling the first portion to the second portion, wherein the output pulley is located on the bell crank linkage.

12. The orthosis of claim 1, wherein rotating the first spool and the second spool to pull at least part of the second portion towards at least part of the first portion comprises rotating the first spool and the second spool in a first direction.

13. The orthosis of claim 12, wherein the actuator is further configured to rotate the first spool and the second spool in a second direction to allow the output pulley to move away from the first portion so as allow the at least part of the second portion to move away from the at least part of the first portion.

14. The orthosis of claim 1, wherein the second spool is configured to feed the belt less than the given length pulled by the first spool due to a diameter of belt turns on the first spool exceeding a diameter of belt turns on the second spool.

15. The orthosis of claim 1, wherein the first spool and the second spool are configured to rotate at a same speed.

16. The orthosis of claim 1, wherein the first spool and the second spool are configured to rotate in a same direction.

17. The orthosis of claim 1, wherein the first spool and the second spool are configured to rotate in opposite directions.

18. The orthosis of claim 1, wherein the belt has a thickness no greater than about 0.005 inches.

19. The orthosis of claim 1, further comprising:
   a motor configured to drive rotation of the first spool and the second spool;
   a drive sprocket connected to the motor; and
   a driven sprocket connected to the first spool, the drive sprocket and the driven sprocket connected by a second belt, the driven sprocket having a larger diameter than the drive sprocket.

20. The orthosis of claim 1, wherein the first portion is configured to attach above the patient's knee and the second portion is configured to attach below the patient's knee.

21. The orthosis of claim 1, further comprising a rotational position sensor coupled to the actuator, wherein the rotational position sensor is configured to communicate with a controller to indicate a position of the first portion relative to the second portion.

22. The orthosis of claim 1, further comprising a belt tensioner, a tensioner position sensor, a spool rotation counter, and a controller, wherein a rotational position of the first portion relative to the second portion is determined by the controller based on the spool rotation counter and belt tensioner position.

23. A harmonic winch, comprising:
   a first spool rotatably mounted to a first housing;
   a second spool rotatably mounted to the first housing;
   an output pulley mounted to a second housing;
   a belt having a first end wrapped around the first spool, a second end wrapped around the second spool, and a mid-portion wrapped around the output pulley; and a motor configured to rotate the first spool and the second spool, the rotation of the first spool pulling the belt a given length and the rotation of the second spool feeding the belt less than the given length so as to pull the output pulley and the second housing towards the first housing.

24. The harmonic winch of claim 23, wherein the actuator further comprises a belt tensioner configured to take up slack in the belt.

25. The harmonic winch of claim 24, wherein the belt tensioner comprises a rotatable disk separate from the first spool, the second spool and the output pulley.

26. The harmonic winch of claim 25, wherein the rotatable disk comprises at least one moving roller configured to interact with at least one fixed roller to increase a belt path length.

27. The harmonic winch of claim 25, wherein the belt tensioner comprises a rotational position sensor coupled to the rotatable disk, and wherein the sensor is configured to communicate with a controller to indicate a belt tension when there is no slack in the belt.

28. The harmonic winch of claim 23, wherein the second spool is configured to feed the belt less than the given length pulled by the first spool due to a diameter of belt turns on the first spool exceeding a diameter of belt turns on the second spool.

29. The harmonic winch of claim 23, wherein the first spool and the second spool are configured to rotate at a same speed.

30. The harmonic winch of claim 23, wherein the first spool and the second spool are configured to rotate in a same direction.

31. The harmonic winch of claim 23, wherein the first spool and the second spool are configured to rotate in opposite directions.

32. The harmonic winch of claim 23, wherein the belt has a thickness no greater than about 0.005 inches.

33. The harmonic winch of claim 23, further comprising:
a motor configured to drive rotation of the first spool and the second spool;
a drive sprocket connected to the motor; and
a driven sprocket connected to the first spool, the drive sprocket and the driven sprocket connected by a second belt, the driven sprocket having a larger diameter than the drive sprocket.

34. A method of assisting movement of a patient, comprising:
attaching a first portion of an orthosis to a patient on one side of a joint;
attaching a second portion of the orthosis to the patient on an opposite side of the joint;
detecting a residual intention of the patient to move the joint; and
assisting the patient with the intended movement by applying an assistive force to the patient with an actuator, the actuator comprising:
a first spool rotatably mounted to the first portion;
a second spool also rotatably mounted to the first portion;
an output pulley mounted to the second portion; and
a belt having a first end wrapped around the first spool, a second end wrapped around the second spool, and a mid-portion wrapped around the output pulley.

35. The method of claim 34, wherein the assisting step comprises rotating the first spool to pull the belt a given length and rotating the second spool to feed the belt less than the given length such that the output pulley on the second portion is pulled towards the first portion of the orthosis.

36. The method of claim 34, wherein the attaching a first portion step comprises attaching the first portion of the orthosis around a thigh of the patient, and the attaching a second portion step comprises attaching the second portion around a calf of the patient.

37. The method of claim 34, wherein the attaching a first portion step comprises attaching the first portion of the orthosis around an upper arm of the patient, and the attaching a second portion step comprises attaching the second portion around a lower arm of the patient.

* * * * *